US008383633B2

(12) United States Patent
Mortimore et al.

(10) Patent No.: US 8,383,633 B2
(45) Date of Patent: Feb. 26, 2013

(54) AMINOPYRIMIDINES USEFUL AS KINASE INHIBITORS

(75) Inventors: Michael Mortimore, Burford (GB); Julian Golec, Faringdon (GB); Daniel Robinson, Abingdon (GB); John Studley, Abingdon (GB)

(73) Assignee: Vertex Pharmaceuticals Incorporated, Cambridge, MA (US)

( * ) Notice: Subject to any disclaimer, the term of this patent is extended or adjusted under 35 U.S.C. 154(b) by 413 days.

(21) Appl. No.: 12/598,276

(22) Filed: Oct. 30, 2009

(65) Prior Publication Data

US 2010/0215772 A1 Aug. 26, 2010

Related U.S. Application Data

(63) Continuation of application No. PCT/US2008/062329, filed on May 2, 2008.

(60) Provisional application No. 60/915,575, filed on May 2, 2007.

(51) Int. Cl.
*C07D 403/12* (2006.01)
*A61K 31/506* (2006.01)

(52) U.S. Cl. ........ 514/256; 514/274; 514/275; 544/317; 544/324; 544/328

(58) Field of Classification Search ................ 544/317, 544/324, 328; 514/256, 274, 275
See application file for complete search history.

(56) References Cited

U.S. PATENT DOCUMENTS

| | | | |
|---|---|---|---|
| 3,133,081 A | 5/1964 | Lafferty et al. |
| 3,755,322 A | 8/1973 | Winter et al. |
| 3,935,183 A | 1/1976 | Baron et al. |
| 3,939,183 A | 2/1976 | Gardner et al. |
| 3,998,951 A | 12/1976 | Harnish et al. |
| 4,051,252 A | 9/1977 | Mayer et al. |
| 4,493,726 A | 1/1985 | Burdeska et al. |
| 4,540,698 A | 9/1985 | Ishikawa et al. |
| 4,711,951 A | 12/1987 | Axen et al. |
| 5,124,441 A | 6/1992 | Carlsson et al. |
| 5,710,158 A | 1/1998 | Myers et al. |
| 5,916,908 A | 6/1999 | Giese et al. |
| 5,972,946 A | 10/1999 | Murata et al. |
| 6,093,716 A | 7/2000 | Davis et al. |
| 6,184,226 B1 | 2/2001 | Chakravarty et al. |
| 6,200,977 B1 | 3/2001 | Cushing et al. |
| 6,277,989 B1 | 8/2001 | Chakravarty et al. |
| 6,495,582 B1 | 12/2002 | Hale et al. |
| 6,528,509 B1 | 3/2003 | Hale et al. |
| 6,528,513 B2 | 3/2003 | Cushing et al. |
| 7,473,691 B2 | 4/2003 | Davies et al. |
| 6,558,657 B1 | 5/2003 | Mandeville, III et al. |
| 6,562,971 B2 | 5/2003 | Frauenkron et al. |
| 6,569,499 B2 | 5/2003 | Grammatica et al. |
| 6,579,983 B1 | 6/2003 | Batchelor et al. |
| 6,589,958 B1 | 7/2003 | Frietze |
| 6,593,326 B1 | 7/2003 | Bradbury et al. |
| 6,610,677 B2 | 8/2003 | Davies et al. |
| 6,613,776 B2 | 9/2003 | Knegtel et al. |
| 6,638,926 B2 | 10/2003 | Davies et al. |
| 6,641,579 B1 | 11/2003 | Bernardi et al. |
| 6,642,227 B2 | 11/2003 | Cao et al. |
| 6,653,300 B2 | 11/2003 | Bebbington et al. |
| 6,653,301 B2 | 11/2003 | Bebbington et al. |
| 6,656,939 B2 | 12/2003 | Bebbington et al. |
| 6,660,731 B2 | 12/2003 | Bebbington et al. |
| 6,664,247 B2 | 12/2003 | Bebbington et al. |
| 6,689,778 B2 | 2/2004 | Bemis et al. |
| 6,696,452 B2 | 2/2004 | Davies et al. |
| 6,716,851 B2 | 4/2004 | Cai et al. |
| 6,727,251 B2 | 4/2004 | Bebbington et al. |
| 6,743,791 B2 | 6/2004 | Cao et al. |
| 6,825,190 B2 | 11/2004 | Moon et al. |
| 6,838,464 B2 | 1/2005 | Pease et al. |
| 6,841,579 B1 | 1/2005 | Plowman et al. |
| 6,846,928 B2 | 1/2005 | Bebbington et al. |
| 6,884,804 B2 | 4/2005 | Choon-Moon |
| 6,919,338 B2 | 7/2005 | Mortlock et al. |
| 6,949,544 B2 | 9/2005 | Bethiel et al. |
| 6,989,385 B2 | 1/2006 | Bebbington et al. |
| 7,008,948 B2 | 3/2006 | Bebbington et al. |
| 7,084,159 B2 | 8/2006 | Cao et al. |
| 7,087,603 B2 | 8/2006 | Bebbington et al. |
| 7,091,343 B2 | 8/2006 | Bebbington et al. |
| 7,098,330 B2 | 8/2006 | Bebbington et al. |
| 7,115,739 B2 | 10/2006 | Bebbington et al. |
| 7,179,826 B2 | 2/2007 | Bebbington et al. |
| 7,253,187 B2 | 8/2007 | Cao et al. |
| 7,304,061 B2 | 12/2007 | Hale et al. |
| 7,345,054 B2 | 3/2008 | Hale et al. |

(Continued)

FOREIGN PATENT DOCUMENTS

DE 2458965 6/1976
EP 0019811 12/1980

(Continued)

OTHER PUBLICATIONS

Caravajal et al., Aurora Kinases: New Targets for Cancer Therapy, Clin Cancer Res 2006:12(23), pp. 6869-6875, Dec. 1, 2006.*
Johnson et al., Relationships between drug activity in NCI preclinical in vitro and in vivo models and early clinical trials, British Journal of Cancer (2001) 64(10): 1424-1431.*
Gura, Systems for identifying New Drugs Are Often Faulty, Cancer Models, Science, vol. 278, No. 5340, pp. 1041-1042, Nov. 1997.*
Simone, Oncology: Introduction, Cecil Textbook of Medicine, 20th Edition, vol. 1, pp. 1004-1010, 1996.*
Rogers et al., PubMed Abstract (J Cell Biol. 157(2):219-29, Epub) Apr. 2002.*
Tanaka et al., PubMed Abstract (Cell 108(3):317-29) Feb. 2002.*

(Continued)

*Primary Examiner* — Deepak Rao
(74) *Attorney, Agent, or Firm* — Rory C. Stewart

(57) ABSTRACT

The present invention relates to compounds useful as inhibitors of Aurora protein kinases. The invention also provides pharmaceutically acceptable compositions comprising those compounds and methods of using the compounds and compositions in the treatment of various disease, conditions, and disorders. The invention also provides processes for preparing compounds of the invention.

35 Claims, No Drawings

U.S. PATENT DOCUMENTS

| | | | |
|---|---|---|---|
| 7,361,665 B2 | 4/2008 | Ledeboer et al. |
| 7,390,815 B2 | 6/2008 | Davies et al. |
| 7,427,681 B2 | 9/2008 | Bebbington et al. |
| 7,491,730 B2 | 2/2009 | Forster et al. |
| 7,528,142 B2 | 5/2009 | Binch et al. |
| 7,531,536 B2 | 5/2009 | Bebbington et al. |
| 7,557,106 B2 | 7/2009 | Charrier et al. |
| 7,579,349 B2 | 8/2009 | Nowak et al. |
| 7,625,913 B2 | 12/2009 | Bebbington et al. |
| 7,691,853 B2 | 4/2010 | Bebbington et al. |
| 7,737,151 B2 | 6/2010 | Mortimore et al. |
| 7,767,672 B2 | 8/2010 | Binch et al. |
| 7,820,685 B2 | 10/2010 | Binch et al. |
| 7,863,282 B2 | 1/2011 | Bebbington et al. |
| 7,872,129 B2 | 1/2011 | Forster et al. |
| 7,951,820 B2 | 5/2011 | Bebbington et al. |
| 7,982,037 B2 | 7/2011 | Bebbington et al. |
| 7,989,456 B2 | 8/2011 | Mortimore et al. |
| 2001/0018436 A1 | 8/2001 | Cushing et al. |
| 2002/0052386 A1 | 5/2002 | Armistead et al. |
| 2002/0065270 A1 | 5/2002 | Moriarty et al. |
| 2003/0004161 A1 | 1/2003 | Bebbington et al. |
| 2003/0004164 A1 | 1/2003 | Bebbington et al. |
| 2003/0022885 A1 | 1/2003 | Bebbington et al. |
| 2003/0036543 A1 | 2/2003 | Bebbington et al. |
| 2003/0055044 A1 | 3/2003 | Davies et al. |
| 2003/0055068 A1 | 3/2003 | Bebbington et al. |
| 2003/0064981 A1 | 4/2003 | Knegtel et al. |
| 2003/0064982 A1 | 4/2003 | Davies et al. |
| 2003/0069239 A1 | 4/2003 | Cai et al. |
| 2003/0069248 A1 | 4/2003 | Chakravarty et al. |
| 2003/0073687 A1 | 4/2003 | Bebbington et al. |
| 2003/0078166 A1 | 4/2003 | Davies et al. |
| 2003/0078275 A1 | 4/2003 | Bebbington et al. |
| 2003/0083327 A1 | 5/2003 | Davies et al. |
| 2003/0087922 A1 | 5/2003 | Bethiel et al. |
| 2003/0092714 A1 | 5/2003 | Cao et al. |
| 2003/0096813 A1 | 5/2003 | Cao et al. |
| 2003/0096816 A1 | 5/2003 | Cao et al. |
| 2003/0105090 A1 | 6/2003 | Bebbington et al. |
| 2003/0144309 A1 | 7/2003 | Choon-Moon |
| 2003/0171389 A1 | 9/2003 | Bemis et al. |
| 2003/0187002 A1 | 10/2003 | Mortlock et al. |
| 2003/0199526 A1 | 10/2003 | Choquette et al. |
| 2003/0207873 A1 | 11/2003 | Harrington et al. |
| 2003/0225073 A1 | 12/2003 | Bebbington et al. |
| 2004/0002496 A1 | 1/2004 | Bebbington et al. |
| 2004/0009974 A1 | 1/2004 | Bebbington et al. |
| 2004/0009981 A1 | 1/2004 | Bebbington et al. |
| 2004/0009996 A1 | 1/2004 | Moon et al. |
| 2004/0023963 A1 | 2/2004 | Cao et al. |
| 2004/0029857 A1 | 2/2004 | Hale et al. |
| 2004/0167141 A1 | 2/2004 | Bebbihngdon et al. |
| 2004/0049032 A1 | 3/2004 | Charrier et al. |
| 2004/0097501 A1 | 5/2004 | Bebbington et al. |
| 2004/0097531 A1 | 5/2004 | Ledeboer et al. |
| 2004/0157893 A1 | 8/2004 | Bebbington et al. |
| 2004/0214814 A1 | 10/2004 | Bebbington et al. |
| 2004/0229875 A1 | 11/2004 | Cao et al. |
| 2005/0004110 A1 | 1/2005 | Bebbington et al. |
| 2005/0038023 A1 | 2/2005 | Bebbington et al. |
| 2005/0049246 A1 | 3/2005 | Bemis et al. |
| 2005/0228005 A1 | 10/2005 | Moon et al. |
| 2005/0234059 A1 | 10/2005 | Hale et al. |
| 2006/0270660 A1 | 11/2006 | Charrier et al. |
| 2007/0179125 A1 | 8/2007 | Fraysse et al. |
| 2007/0190634 A1 | 8/2007 | Bebbington et al. |
| 2007/0265263 A1 | 11/2007 | Cao et al. |
| 2008/0287444 A1 | 11/2008 | Bebbington et al. |
| 2009/0181938 A1 | 7/2009 | Binch et al. |
| 2009/0221602 A1 | 9/2009 | Charrier et al. |
| 2010/0022502 A1 | 1/2010 | Jimenez et al. |
| 2010/0022507 A1 | 1/2010 | Jimenez et al. |
| 2010/0137305 A1 | 6/2010 | Binch et al. |
| 2010/0215772 A1 | 8/2010 | Mortimore et al. |
| 2010/0267768 A1 | 10/2010 | DeMattei et al. |
| 2010/0310675 A1 | 12/2010 | Binch et al. |
| 2010/0317641 A1 | 12/2010 | Mortimore et al. |
| 2011/0020376 A1 | 1/2011 | Jimenez et al. |
| 2011/0020377 A1 | 1/2011 | Pierce et al. |
| 2011/0020469 A1 | 1/2011 | Binch et al. |
| 2011/0021559 A1 | 1/2011 | Jimenez et al. |
| 2011/0046104 A1 | 2/2011 | Mortimore et al. |
| 2011/0060013 A1 | 3/2011 | Mortimore et al. |
| 2011/0086856 A1 | 4/2011 | Bebbington et al. |
| 2011/0269732 A1 | 11/2011 | Golec et al. |

FOREIGN PATENT DOCUMENTS

| | | |
|---|---|---|
| EP | 00198811 | 12/1980 |
| EP | 0136976 | 4/1985 |
| EP | 136976 | 4/1985 |
| EP | 0302312 | 2/1989 |
| GB | 2052487 | 1/1981 |
| JP | 06065237 | 3/1994 |
| JP | 10-130150 | 5/1998 |
| JP | 10130150 | 5/1998 |
| JP | 2000-026421 | 1/2000 |
| JP | 2000026421 | 1/2000 |
| JP | 06-65237 | 10/2007 |
| WO | 9208715 | 5/1992 |
| WO | 9322681 | 11/1993 |
| WO | 9509851 | 4/1995 |
| WO | 9515758 | 6/1995 |
| WO | 9614843 | 5/1996 |
| WO | 9709325 | 3/1997 |
| WO | 9719065 | 5/1997 |
| WO | 9802434 | 1/1998 |
| WO | 9811095 | 3/1998 |
| WO | 9814450 | 4/1998 |
| WO | 9816502 | 4/1998 |
| WO | 9838171 | 9/1998 |
| WO | 9918781 | 4/1999 |
| WO | 9941253 | 8/1999 |
| WO | 9947154 | 9/1999 |
| WO | 9962518 | 12/1999 |
| WO | 9965897 | 12/1999 |
| WO | 0012497 | 3/2000 |
| WO | 0021955 | 4/2000 |
| WO | 0039101 | 6/2000 |
| WO | 0038675 | 7/2000 |
| WO | 0039101 | 7/2000 |
| WO | 0042029 | 7/2000 |
| WO | 0059509 | 10/2000 |
| WO | 0078757 | 12/2000 |
| WO | 0112621 | 2/2001 |
| WO | 0125220 | 4/2001 |
| WO | 0144242 | 5/2001 |
| WO | 0139777 | 6/2001 |
| WO | 0140215 | 6/2001 |
| WO | 0144242 | 6/2001 |
| WO | 0147879 | 7/2001 |
| WO | 0147897 | 7/2001 |
| WO | 0160816 | 8/2001 |
| WO | 0164655 | 9/2001 |
| WO | 0174768 | 10/2001 |
| WO | 0179198 | 10/2001 |
| WO | 0174768 | 11/2001 |
| WO | 0125220 | 12/2001 |
| WO | 0208244 | 1/2002 |
| WO | 0218346 | 3/2002 |
| WO | 0222601 | 3/2002 |
| WO | 0222602 | 3/2002 |
| WO | 0222603 | 3/2002 |
| WO | 0222604 | 3/2002 |
| WO | 0222605 | 3/2002 |
| WO | 0222606 | 3/2002 |
| WO | 0222607 | 3/2002 |
| WO | 0222608 | 3/2002 |
| WO | 0224667 | 3/2002 |
| WO | 0247690 | 6/2002 |
| WO | 0250065 | 6/2002 |
| WO | 0250066 | 6/2002 |
| WO | 02057259 | 7/2002 |
| WO | 02059111 | 8/2002 |
| WO | 02059112 | 8/2002 |
| WO | 02062789 | 8/2002 |
| WO | 02066461 | 8/2002 |

| WO | 02068415 | 9/2002 |
| WO | 02079197 | 10/2002 |
| WO | 03026664 | 4/2003 |
| WO | 03077921 | 9/2003 |
| WO | 03078426 | 9/2003 |
| WO | 03078427 | 9/2003 |
| WO | 04000833 | 12/2003 |
| WO | 200400833 | 12/2003 |
| WO | 2004000833 A1 | 12/2003 |
| WO | 200413140 | 2/2004 |
| WO | 2004013140 | 2/2004 |
| WO | 2004037814 | 5/2004 |
| WO | 2007041358 | 9/2005 |
| WO | 2007023382 | 1/2007 |
| WO | 2007041358 | 4/2007 |
| WO | 2007056163 A | 5/2007 |
| WO | 2007056164 A | 5/2007 |
| WO | 2007056164 A1 | 5/2007 |
| WO | 2007059299 | 5/2007 |
| WO | WO 2007/056221 * | 5/2007 |
| WO | 2008057940 | 5/2008 |
| WO | 9838171 | 1/2012 |

OTHER PUBLICATIONS

Rouse, J. et al., "A Novel Kinase Cascade Triggered by Stress and Heat Shock That Stimulates MAPKAP Kinase-2 and Phosphorylation of the Small Heat Shock Proteins," Cell, 78, 1027-1037 (1994).
Rueeger, H. et al, "Design, synthesis and SAR of a series of 2-substituted 4-amino-quinazolineneuropeptide Y Y5 receptor antagonists," Bioor. Med. Chem. lett., 10(11), 1175-1180 (2000).
Shikhaliev, K.S. et al., "Heterocyclization of quinazol-2-ylguanidines. 1. Reaction with amino acids", Chem. Heterocycl. Compd. 35 (7), 818-820 (1999).
Simone, J.V., "Oncology Introduction" in Cecil Textbook in Medicine, 20th ed. vol. 1, 1004-1010 (1996).
Singh, S.P. et al., "Synthesis & Mass Spectra of Some Substituted 2-(2'-Benzazolylamino)pyrimidines", Indian J. Chem. Sect. B, 22(1): 37-42 (1983).
Singhal, N. et al., "Synthesis and Antimalarial Activity of Some New Quinazoline Derivatives", Indian Chem. Soc. 61, 690-693 (1984).
Sivaraman, V.S. et al., "Hyperexpression of Mitogen-activated Protein Kinase in Human Breast Cancer", J. Clin. Invest., 99(7), 1478-1483 (1997).
Soriano, P. et al., ed Disruption of the C-SRC Proto-Ocogene Leads to Osteopetrosis in Mice, Cell, 64: 693-702 (1991).
Staley, C.A. et al., "Decreased Tumorigenicity of a Human Colon Adenocarcinoma Cell Line by an Antisense Expression Vector Specific for c-Src," Cell Growth Diff., 8 269-274 (1997).
Suzuki, S. et al., "Application of electrogenerated triphenylmethyl anion as a base for alkylation of arylacetic esters and arylacetonitrites and isomerization of allylbenzenes," Can. J. Chem., 72(2): 357-361 (1994).
Takashima, K. et al., "Tau Protein Kinase I is Essential for Amyloid β-Protein-Induced Neurotoxicity," PNAS 90, 7789-7793 (1993).
Takayanagi, H. et al., "Suppression of arthritic bone destruction by adenovirus-mediated csk gene transfer to synoviocytes and osteoclasts," J. Clin. Invest., 104, 137-146(1999).
Talamonti, M.S. et al., "Increase in activity and level of pp60c-src in progressive stages of human colorectal cancer," J. Clin Invest., 91(1): 53-60 (1993).
Tanji, K. et al., "Purines. X. Reactivities of Methyl Groups on 9-Phenylpurines: Condensation with an Aldehyde or an Ester, and Oxidation with Selenium Dioxide," Chem. Phar. Bull., 40 (1), 227-229 (1992).
The Condensed Chemical Dictionary, Sixth Edition h Rose, 38 by Arthur and Elizabeth Rose, 38 (1961).
Ti, J. et al., "Anticandidal activity of pyrimidine-peptide conjugates," J. Med. Chem., 23(8), 913-918 (1980).
Toriyabe, Keiji et al., "Preparation of sulfur-containing arylthiazoles and insecticides," Chemica Abstracts, 132(8): 93314 (2000).
Traxier P. et al., "Use of a pharmacophonre model for the design of EGF-R Tyrosine Kinase Inhibitors: 4-(Phenylamino)Pyrazolo[3,4-d]pyrimidines," Journal of Medicinal Chemistry, 40(22): 3601-3616 (1997).

Venugopalan, B. et al., "Synthesis and antimalarial activity of pyrido[3,2-f)quinozalines and their N-oxides," Indian J. Chem. Sect. B, 34, 9, 779-790 (1995).
Wagman, A.S. et al., "Discovery and Development of GSK3 Inhibitors for the Treatment of Type 2 Diabetes," Current Pharmaceutical Design, 10, 1105-1137 (2004).
Warner, S.L. et al., "Targeting Aurora-2 Kinase in Cancer," Mol. Cancer Thera., 2, 589-585, 2003.
Whelchel, A. et al., "Inhibition of ERK Activation Attenuates Endothelin-stimulated Airway Smooth Muscle Cell Proliferation," Am. J. Respir. Cell Mol. Biol., 16, 589-596 (1997).
Wiener, J.R., "Decreased Src Tyrosine Kinase Activity Inhibits Malignant Human Ovarian Cancer Tumor Growth in a Nude Mouse Model," Clin. Cancer Res., 5, 2164-2170 (1999).
Wolft, Manfred E., "Burger's Medicinal Chemistry, 1" 5th ed., Part 1 John Wiley & Sons, 1995, pp. 975-977.
Yuan, Z.Q. et al., "Frequent activation of AKT2 and induction of apoptosis by inhibition of phosphoinositide-3-OH kinase/Akt pathway in human ovarian cancer," Oncogene, 19, 2324-2330 (2000).
Zhang, Z. et al., "Destabilization of β-catenin by mutations in presenilin-1 potentiates neuronal apoptosis," Nature, 395, 698-702 (1998).
Office Action from U.S. Appl. No. 10/026,992, mailed May 22, 2008.
International Search Report, PCT/US2008/062329, filed Sep. 10, 2008.
Hamdane, M. et al., "Pin 1—A Therapeutic Target in Alzheimer Neurodegeneration," J. Mol. Neurosci., 19(3): 275:87 (2002).
Haq. S. et al., "Glycogen Synthase Kinase-3β Is a Negative Regulator of Cardiomyocyte Hypertrophy", J. Cell Biol., 151(1), 177-129 (2000).
Hardt, S.E., et al., "Glycogen Synthase Kinase-3β—A Novel Regulator of Cardiac Hypertrophy and Development," Circulation Research, 90: 1055-1063 (2002).
Haworth, R D et al. "Synthetic antimalarials. Part XXVII. Some derivatives of phthalazine, quinoxaline, and isoquinoline", J. Chem. Soc., 777-782 (1948).
Heaney, F., et al., "Pyrimidine annelated heterocycles-synthesis and cycoaddition of the first pyrimido[1,4]diazepine N-oxides," J. Chem. Soc., Perkin Trans., 1:622-632 (2001).
IUPAC Compendium of Chemical Terminology on a definition of "aliphatic compounds" found from http://www.chemsoc.org/chembytes/goldbook/index.htm (last visited on Nov. 18, 2007).
Ivashchenko A.V. et al., "Synthesis and Study of Heteroaromatic Ligands Containing a Pyrimidine Ring", Khim. Geterotsikl. Soedin., (12), 1673-7, (1980).
Jambhekar, S.S., "Biopharmaceutical Properties of Drug Substances" in Principles of Medicinal Chemistry, 4th ed., 12-24 (1995).
Jeffrey, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).
Katzung, Bertram G., Basic and Clinical Pharmacology, 7th Edition, 1998, pp. 881-884.
Kelarev, V.I. et al., "Synthesis of amino derivatives of 1,3,5-triazine containing 1,3-4-thiadiazole fragments," Izvestiya Vysshikh Uchebnkh Zavedenii, Khimiya I Khimicheskaya Tekhnologiya, 40(5):27-32 (1997).
Kim, L. et al., "GSK3, a master switch regulating cell-fate specification and tumorigenesis" Current Opinion in Genetics & Development, 10:508-514 (2000).
Kim, Y.Z. et al., "Synthesis and Antimicrobial Activity of Novel [)3-Aminopyrimidiniumyl)thio]methyl Cephalosporins", J. Med. Chem., 37(22); 3828-3833 (1994).
Kimura M. et al., "Cell Cycle-dependent Expression and Centrosome Localization of a Third Human Aurora/Ipl1-related Protein Kinase, AIK3", J. Biol. Chem., 274(11), 7334-7340 (1999).
Klein, P.S. et al., "A molecular mechanism for the effect of lithium on development", PNAS, 93:8455-8459 (1996).
Lee, S.j. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med. Chem., 38 (18):3547-3557 (1995).

Lübbers, T. et al., "Design synthesis, and structure-activity relationship studies of ATP analogues as DNA gyrase inhibitors", Bioorg. Med. Chem. Lett., 10, 8, 821-826 (2000).

Lutz M.L. et al., "Overexpression and Activation of the Tyrosine Kinase Src in Human Pancreatic Carcimona", Biochem. Biophys. Res. 243, 503-508 (1998).

Lyrer, P., Schweiz. "Neue Ansätze in der Akutbehandlung des zerebrovaskulären Insultes." Med. Woohen Schr., 124 (45); 2005-2012 (1994).

Mani, S. et al., "Cyclin-dependent kinase: novel anticancer agents", Exp. Opin. Invest. Drugs, 8, 1849-1870 (2000).

Medwid, Jeffrey B. et al., "Preparation of triazolo'1, 5-cipyrimidines as potential antiasthma agents," J. Med. Chem., 33 (4): 1230-1241 (1990).

Molina, T.J. et al., "Profound block in thymocyte development in mice lacking p56Ick", Nature, 357, 161-164 (1992).

Moodie, S.A. et al., "Complexes of Ras-GTP with Raf-1 and Mitogen-Activated Protein Kinase", Science, 260 (5114), 1658-1661 (1993).

Myers, M. R. et al., "The synthesis and SAR of new 4-(N-alkyl-N-phenyl)amino-6,7-dimethoxyquinazolines and 4-(N-alkyl-N-Phenyl)aminopyrazolo[3,4-d]pyrimidines, inhibitors of CSF-1R tyrosine kinase activity", Bioorg. Med. Chem. Lett., 7, 4, 421-424 (1997).

Nair, M.D., et al., "3-Chloroisocarbostyril & Its Chlorination Products", Indian J. Chem., vol. 5, 467-470 (1967).

Namikawa, Kazuhiko et al., "Akt/Protein Kinase B Prevents Injury-Induced Motoneuron Death and Accelerates Axonal Regeneration," The Journal of Neuroscience, 20(8), 2875-2886 (2000).

Nezu, Y. et al., "Dimethoxypyrimidines as Novel Herbicides, part 1. Synthesis and Herbicidal Activity of Dimethoxyphanoxyphenoxypyrimidines and Analogues," Pestic. Sci., 47(2): 103-113 (1996).

Nezu, Y., et al., "Dimethoxypyrimidines as Novel Herbicides, part 2. Synthesis and Herbicidal Activity of O-Pyrimidinylasalicylates and Analogues," Pestic. Sci., 47(2): 115-124 (1996).

Norman, M.H. et al., "Structure-Activity Relationships of a Series of Pyrrolo[3,2-d]pyrimidine Derivatives and Related Compounds as Neuropeptide Y5 receptor Antagonists," J. Med. Chem., 43(22), 4288-4312 (2000).

Nugent, R.A. et al., "Pyrimidine Thiotheters: A Novel Class of HIV-1 Reverse Transcriptease Inhibitors with Activity Against BHAP-Resistant HIV", J. Med. Chem., 41, 3793-3803 (1998).

Okafor, Charles O., "Studies in the Heterocyclic Series. 1,3,9-Triazaphenothiazine Ring System, A New Phenothiazine Ring," J. Org. Chem., 40(19):2753-2755 (1975).

Pei, J. et al., "Distribution, Levels and Activity of Glycogen Synthase Kinase-3 in the Alzheimer Disease Brain", J. Neuropathol. Exp. Neurology, 56, 70-78 (1997).

Prasad, G. et al., "18-Crown-6 as a catalyst in the dialkylation of o-nitrophenacyl derivatives," J. Org. Chem., 25, 7188-7190 (1991).

Raingeaud, J. et al., "MMK3- and MMK6-Regulated Gene Expression Is Mediated by p38 Mitogen-Activated Protein Kinase Signal Transduction Pathway," Mol. Cell. Biol. 16, 1247-1255 (1996).

Rogers, E., et al., "The aurora kinase AIR-2 functions in the release of chromosome cohesion in Caenorhabditis elegans meiosis," J. Cell Biol., 157(2): 219-229 (2002).

Rosen, N. et al., "Analysis of pp60src Protein Kinase Activity in Human Tumor Cell Lines and Tissues," J. Biol. Chem., 261, 13754-13759 (1986).

Agarwal, N. et al., "Suitably Functionalized Pyrimidines as Potential Antimycotic Agents", Bioorg. Med. Chem. Ltt., 10, 8, 703-706 (2000).

Ali, N.m. et al., "Palladium-Catalyzed Cross Coupling Reactions of Arylboronic Acids with Pi-Deficient Heteroaryl Chlorides" Tetrahedron, 48 (37), 8117-8126 (1992).

Anderson, Neil G. "Requirement for integration of signals from two distinct phosphorylation pathways for activation of MAP kinase." Nature, 343, 651-653 (1990).

Anonymous, "Vertex Inhibitors of Aurora-2, glycogen synthase kinase-3 and Src Kinase", Expert Opin. Ther. Patents 14(3): 439-443 (2004).

Bai, G.U. et al., "Triazines and Related Products. Part 28' Conversion of 3-Aryl-1-(2-cyanophenyl) triazenes into 3-Arlquinazolin-4(3H)-ones with Formamide" J. Chem. Soc. Perkin Trans. I, 2765-2766 (1984).

Baig, Ghouse Unissa et al. "Triazines and related products. Part 27. Thermolysis of 4-anilino-1,2,3-benzotriazines," J. Chem., Soc., Perkin Trans. 1(5): 999-1003 (1984).

Banker, G.S. et al., "Modern Pharmaceutics", 34d ed., Marcel Dekker, New York 1996, pp. 451 & 596.

Biagi, G. et al., Synthesis of 4,6-Distributed and 4,5,6-Trisubstituted-2-Phyl-pyrimidines and their Affinity Towards A1 Adenosine Receptors, IL Farmaco., 52(1), 61-65 (1997).

Bischoff, J.R. et al., "A homologue of Drosophila aurora kinase is oncogenic and amplified in human colorectal cancers", the EMBO Journal, 17(11): 3052-3065 (1998).

Bjorbaek, c. et al., "Divergent Functional Roles for p90rsk Kinase Domains", J. Biol. Chem., 270(32, 19948-19552 (1995).

Bokemeyer, D. et al., "Multiple intracellular MAP kinase signaling cascades", Kidney Int, 49, 1187-1198 (1996).

Boschelli et al., "Small molecule inhibitors of Src family kinases", Drugs of the Future, 25(7):717-736 (2000).

Brownlees J. et al., "Tau phosphorylation in transgenic mice expressing glycogen synthase kinase-3beta transgenes", Neuroreport., 8(15), 3251-5 (1997).

Brunswick, D.J. et al., "Cyclic Amidines. Part XXII. Novel Isomerism of Disubstituted Tricycioquinazolines and Molecular Orientations in Carcinogenesis", J. Chem. Soc. (3), 2641-2647 (1970).

Campbell, S.F. et al., "2,4-Diamino-6,7-dimethoxyquinazolines. 3.2(4-Heterocyclylpiperazin-l-yl) Derivatives as αl-Adrenoceptor Antagonists and Antihypertensive Agents," J. Med Chem., 30, 1794-1798 (1987).

CAPLUS listing Accession No. 1994:292136, Nakajima, Y. et al., "Pyrazoles agricultural and horticultural bactericides," JP 06065237 (1994).

Casanova, B. et al., "revision critica de la patogenia actual de la esclerosis multiple y futuras direcciones posibles," Rev. Neurol., 28 (9): 909-915 (1999).

Chalmers, D.T., et al., "Corticotrophin-releasing factor receptors: from molecular biology to drug design," TiPS, 17, 769-776 (2001).

Charpiot, B. et al., "Quinazolines: Combined type 3 and 4 phosphodiesterase inhibitors", Bioorg. Med. Chem. Lett., 8 (20), 2891-2896 (1988).

Chen, R.H. et al., "Phosphorylation of the c-Fos transrepression domain by mitogent-activated protein kinase and 90-kDa ribosomal S6 kinase", Proc. Natl. Acad. Sci. USA, 90, 10952-10956 (1993).

Coghlan, M.P. et al., "Selective small molecule inhibitors of glycogen synthase kinase-3 modulate glycogen metabolism and gene transcription", Chemistry & Biology, 7, 793-803 (2000).

Cohen, P. et al., "The renaissance of GSK3," Nat. Rev. Mol. Cell Biol., 2, 769-776 (2001).

Cohen, P. "Dissection of the Protein Phosphorylation Cascades Involved in Insulin and Growth Factor Action", Biochem. Soc. Trans., 21-555-567 (1993).

Crespo, M.I., et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).

Curd, F.H.S. et al., "Synthetic antimalarials. Part XVII. Some aminoalkylaminoquinoline derivatives", J. Chem. Soc. 899-909 (1947).

Damasio, A.R., "Alzheimer's Disease and Related Dementias," in Cecil Textbook of Medicine, 20th ed., 2:1992-1996 (1996).

Douglas, et al., "Introduction to Viral Disease" in Cecil Textbook of Medicine, 20th Ed., vol. 2, 1739-1749 (1996).

Eldar-Finkelman, H. et al., "Challenges and opportunities with glycogen synthase kinase-3 inhibitors for insulin resistance and type 2 diabetes treatment," Expert Opinion on Investigation Drugs, 12(9): 1511-1519 (2003).

Fedorynski, M. et al., "Synthesis of 1-Arycyclopropanecarbonitriles under Phase-transfer Cataylist Conditions", Org. Prep. Proced. Int., 27(3), 355-359 (1995).

Fischer, P.M. et al., "inhibitors of Cyclin-Dpendent Kinases as Anti-Cancer Therapeutics", Current Med. Chem., 7, 1213-1245 (2000).

Fischer A., "Therapeutic Strategies in Alzheimer's Disease: M1 Muscarinic Agonists," Jpn. J. Pharmacol., 84(2):101-12 (2000).
Fox T. et al., "A single amino acid substitution makes ERK2 susceptible to pyridinyl imidazole inhibitors of p38 MAP kinase", Protein Sci., 7:2249-2255 (1998).
Frame, M.C., "Src in cancer: deregulation and consequences for cell behaviour," Biochimica et Biophysica Acta, 1602, 114-130 (2002).
Frampton, J.E. et al., "Pentoxifyline (Oxpentifylline)—A Review of its Therapeutic Efficacy in the Management of Peripheral Vascular and Cerebrovascular Disorder," Drugs & Aging, 7(6): 480-503 (1995).
Frey, R.S. et al., "Involvement of Extracellular Signal-regulated Kinase 2 and Stress-activated Protein Kinase/Jun N-Terminal Kinase Activation by Transforming Growth Factor β in the Negative Growth Control of Breast Cancer Cells", Cancer Res., 57, 628-633 (1997).
Garigipati, R.S., "An efficient conversion of nitriles to amidines", Tetrahedron Lett., 31(14)., 1969-1972 (1990).
Gerschon, H. et al., "Pyrimidines 7. A Study of the Chlorination of Pyrimidines with Phosphorous Oxychloride in the Presence of N,N-Dimethylaniline", J. Heterocyclic Chem., 21, 1161-1167 (1984).
Gershon, H. et al., "Pyrimidines. 7. A Study of the Chlorination of Pyrimidines with Phosphorus Oxychloride in the Presence of N,N-Dimethylaniline", J. Heterocyclic Chem., 21, 1161-1167 (1984).
Ife, R.J. et al., "Reversible Inhibitors of the Gastric (H+/K+)-ATPase. 5. Substituted 2,4-Diaminoquinazolines and Thienopyrimidines", J. Med. Chem., 38(14); 2763-2773 (1995).
Tanji, K. et al., "Purines. X. Reactivities of Methyl Groups on 9-Phenylpurines : Condensation with an Aldehyde or an Ester, and Oxidation with Selenium Dioxide", Chem. Phar. Bull., 40 (1), 227-229 (1992).
Charpiot, B. et al., "Quinazolines: Combined type 3 and 4 phosphodiesterase inhibitors", Bioorg. Med. Chem. Lett., 8 (20), 2891-2896 (1998).
Shikhaliev, K.S. et al., "Heterocyclization of quinazol-2-ylguanidines. 1. Reaction with amino acids", Chem. Heterocycl. Compd., 35 (7), 818-820 (1999).
Singh, S.P. et al., "Synthesis & Mass Spectra of Some Substituted 2-(2'-Benzazolylamino)pyrimidines", Indian J. Chem. Sect. B, 22(1); 37-42 (1983).
Ti, J. et al., "Anticandidal activity of pyrimidine-peptide conjugates", J. Med. Chem., 23(8), 913-918 (1980).
Kretzschmar, E. et al., "Synthese von 2,6-disubstituierten 4-Hydroxy-5,6,7,8-tetrahydropyrido[4,3-d]pyrimidinen", Pharmazie, 43(7), 475-476 (1988).
Norman, M.H. et al., "Structure-Activity Relationships of a Series of Pyrrolo[3,2-d]pyrimidine Derivatives and Related Compounds as Neuropeptide Y5 Receptor Antagonists", J. Med. Chem., 43(22), 4288-4312 (2000).
Nugent, R.A. et al., "Pyrimidine Thioethers: A Novel Class of HIV-1 Reverse Transcriptase Inhibitors with Activity Against BHAP-Resistant HIV", J. Med. Chem., 41, 3793-3803 (1998).
Myers, M.R. et al., "The synthesis and SAR of new 4-(N-alkyl-N-phenyl)amino-6,7-dimethoxyquinazolines and 4-(N-alkyl-N-phenyl)aminopyrazolo[3,4-d]pyrimidines, inhibitors of CSF-1R tyrosine kinase activity", Bioorg. Med. Chem. Lett., 7, 4, 421-424 (1997).
Agarwal, N. et al., "Suitably functionalised pyrimidines as potential antimycotic agents", Bioorg. Med. Chem. Lett., 10, 8, 703-706 (2000).
Crespo, M.I. et al., "Design, Synthesis, and Biological Activities of New Thieno[3,2-d]pyrimidines as Selective Type 4 Phosphodiesterase Inhibitors", J. Med. Chem., 41 (21), 4021-4035 (1998).
Noell, C.W. et al., "Potential Purine Antagonists. XX. The Preparation and Reactions of Some Methylthiopurines", J. Am. Chem. Soc., 81(22), 5997-6007 (1959).
Lubbers, T. et al., "Design, synthesis, and structure-activity relationship studies of ATP analogues as DNA gyrase inhibitors", Bioorg. Med. Chem. Lett., 10, 8, 821-826 (2000).
D'Atri, G. et al., "Novel pyrimidine and 1,3,5-triazine hypolipemic agents", J. Med. Chem. 27(12), 1621-1629 (1984).

Venugopalan, B. et al., "Synthesis and antimalarial activity of pyrido[3,2-f]quinozalines and their oxides", Indian J. Chem. Sect. B, 34, 9, 778-790 (1995).
Curd, F.H.S. et al, "Synthetic antimalarials. Part XVII. Some aminoalkylaminoquinoline derivatives", J. Chem. Soc., 899-909 (1947).
Haworth, R.D. et al., "Synthetic antimalarials. Part XXVII. Some derivatives of phthalazine, quinoxaline, and isoquinoline", J. Chem. Soc., 777-782 (1948).
Nair, M.D., et al., "3-Chloroisocarbostyril & Its Chlorination Products", Indian J. Chem., 467-470 (1967).
Jeffery, J.E. et al., "Synthesis of sibutramine, a novel cyclobutylalkylamine useful in the treatment of obesity, and its major human metabolites", J. Chem. Soc., Perkin Trans. 1, 21, 2583-2589 (1996).
Gnecco, D. et al., "An Improved Preparation of 1-Methyl-4-Cyano-4-phenylpiperidine", Org. Prep. Proced. Int., 18 (4), 478-480 (1996).
Fedorynski, M. et al., "Synthesis of 1-Arycyclopropanecarbonitriles under Phase-transfer Catalytic Conditions", Org. Prep. Proced. Int., 27(3), 355-359 (1995).
Suzuki, S. et al., "Application of electrogenerated triphenylmethyl anion as a base for alkylation of arylacetic esters and arylacetonitriles and isomerization of allylbenzenes", Can. J. Chem., 72(2): 357-361 (1994).
Prasad, G. et al., "18-Crown-6 as a catalyst in the dialkylation of o-nitrophenacyl derivatives", J. Org. Chem., 25, 7188-7190 (1991).
Moss, R.A. et al., "Conversion of 'Obstinate' Nitriles to Amidines by Garigipati's Reaction", Tetrahedron Lett., 36(48), 8761-8764 (1995).
Garigipati, R.S., "An efficient conversion of nitriles to amidines", Tetrahedron Lett., 31(14), 1969-1972 (1990).
Warner, S.L. et al, "Targeting Aurora-2 Kinase in Cancer," Mol. Cancer Thera., 2, 589-585, 2003.
Wagman, A.S. et all, "Discovery and Development of GSK3 Inhibitors for the Treatment of Type 2 Diabetes," Current Pharmaceutical Design, 10, 1105-1137 (2004).
Nezu, Y. et al., "Dimethoxypyrimidines as Novel Herbicides. Part 2. Synthesis and Herbicidal Activity of Dimethoxyphenoxyphenoxypyrimidines and Analogues," Pestic. Sci., 47: 115-124 (1996).
Tanaka, T.U. et al., "Evidence that the Ipl1-Sli15 (Aurora Kinase-INCENP) Complex Promotes Chromosome Bi-orientation by Altering Kinetochore-Spindle Pole Connections," Cell, 108, 317-329 (2002).
Soriano, P. et al., "Targeted Disruption of the C-SIC Pmto-Oncogene Leads to Osteopetrosis in Mice," Cell, 64: 693-702, (1991).
Campbell, S.F. et al., "2,4-Diamino-6,7-dimethoxyquinazolines. 3.2-(4-Heterocyclylpiperazin-l-yl) Derivatives as α1-Adrenoceptor Antagonists and Antihypertensive Agents," J. Med. Chem., 30, 1794-1798 (1987).
Casanova, B. et al., "Revisión crítica de la patogenia actual de la esclerosis múltiple y futuras direcciones posibles," Rev. Neurol., 28 (9): 909-915 (1999).
Cline, G.W. et al., "Effects of a Novel Glycogen Synthase Kinase-3 Inhibitor on Insulin-Stimulated Glucose Metabolism in Zucker Diabetic Fatty (fa/fa) Rats," Diabetes, 51, 2903-2910 (2002).
Simone, J.V., "Oncology: Introduction" in Cecil Textbook in Medicine, 20th ed., vol. 1, 1004-1010 (1996).
Coleman, R.A., "The Biological Evaluation of New Compounds" in Medicinal Chemistry: Principles and Practice, King, Frank D. ed, Royal Society of Chemistry, 53-66 (1994).
The Condensed Chemical Dictionary, Sixth Edition by Arthur and Elizabeth Rose, 38 (1961).
Damasio, A.R., "Alzheimer's Disease and Related Dementia," in Cecil Textbook of Medicine, 20th ed., 2: 1992-1996 (1996).
Rogers, E. et al., "The aurora kinase AIR-2 functions in the release of chromosome cohesion in Caenorhabditis elegans meiosis," J. Cell Biol., 157(2): 219-229 (2002).
Fisher A., "Therapeutic Strategies in Alzheimer's Disease: M1 Muscarinic Agonists," Jpn. J. Pharmacol., 84(2):101-12 (2000).
Frame, M.C., "Src in cancer: deregulation and consequences for cell behaviour," Biochimica et Biophysica Acta., 1602, 114-130 (2002).

Frampton, J.E. et al., "Pentoxifylline (Oxpentifylline)—A Review of its Therapeutic Efficacy in the Management of Peripheral Vascular and Cerebrovascular Disorder," Drugs & Aging, 7(6): 480-503 (1995).

Ganellin, C.R., "Past Approaches to Discovering New Drugs as Medicines" in Medicinal Chemistry, Principles and Practices. King, Frank D. ed, Royal Society of Chemistry, 189-205 (1994).

Hamdane, M. et al., "A Therapeutic Target in Alzheimer Neurodegeneration," J. Mol. Neurosci., 19(3): 275-87 (2002).

Hardt, S.E. et al., "Glycogen Synthase Kinase-3β—A Novel Regulator of Cardiac Hypertrophy and Development," Circulation Research, 90: 1055-1063 (2002).

Parnell, E.W., "2-Cyano-4-nitrophenylhydrazine and 3-Amino-5-nitroindazole", J. Chem. Soc., 2363-2365 (1959).

Heaney, F. et al., "Pyrimidine annelated heterocycles—synthesis and cycloaddition of the first pyrimido[1,4]diazepine N-oxides," J. Chem. Soc., Perkin Trans. 1, 622-632 (2001).

Henriksen, E.J. et al., "Modulation of muscle insulin resistance by selective inhibition of GSK-3 in Zucker diabetic fatty rats," Am. J. Physiol. Endocrinol. Metab., 284: E892-E900 (2003).

Okafor, C.O., "Studies in the Heterocyclic Series. X. 1,3,9-Triazaphenothiazine Ring System, a New Phenothiazine Ring," J. Org. Chem., 40(19): 2753-2755 (1975).

Jambhekar, S.S., "Biopharmaceutical Properties of Drug Substances" in Principles of Medicinal Chemistry, 4th ed., 12-24, (1995).

Layzer, R.B., "Section Five—Degenerative Diseases of the Nervous System" in Cecil Textbook of Medicine, 20th ed., 2: 2050-2057 (1996).

Lee, S.J. et al., "Discovery of Potent Cyclic GMP Phosphodiesterase Inhibitors. 2-Pyridyl- and 2-Imidazolylquinazolines Possessing Cyclic GMP Phosphodiesterase and Thromboxane Synthesis Inhibitory Activities," J. Med . Chem., 38 (18): 3547-3557 (1995).

Medwid, J.B. et al., "Preparation of Triazolo[ 1,5-c]pyrimidines as Potential Antiasthma Agents," J. Med. Chem. 33, 1230-1241 (1990).

Nezu, Y. et al., "Dimethoxypyrimidines as Novel Herbicides. Part 1. Synthesis and Herbicidal Activity of Dimethoxyphenoxyphenoxypyrimidines and Analogues," Pestic. Sci., 47: 103-113 (1996).

Cohen, P., "Dissection of the Protein Phosphorylation Cascades Involved in Insulin and Growth Factor Action", Biochem. Soc. Trans., 21, 555-567 (1993).

Haq, S. et al., "Glycogen Synthase Kinase-3β Is a Negative Regulator of Cardiomyocyte Hypertrophy", J. Cell Biol., 151(1), 117-129 (2000).

Fischer, P.M. et al., "Inhibitors of Cyclin-Dependent Kinases as Anti-Cancer Therapeutics", Current Med. Chem., 7, 1213-1245 (2000).

Mani, S. et al., "Cyclin-dependent kinase: novel anticancer agents", Exp. Opin. Invest. Drugs., 8, 1849-1870 (2000).

Fry, D.W. et al., "Inhibitors of cyclin-dependent kinases as therapeutic agents for the treatment of cancer", Current Opin. Oncol. Endoc. & Metab. Investig., 2-40-59 (2000).

Bokemeyer, D. et al., "Multiple intracellular MAP kinase signaling cascades", Kidney Int., 49, 1187-1198 (1996).

Anderson, N. G. et al., "Multiple intracellular MAP kinase signaling cascades", Nature, 343, 651-653 (1990).

Crews, C.M. et al., "The Primary Structure of MEK, a Protein Kinase That Phosphorylates the ERK Gene Product", Science, 258, 478-480 (1992).

Bjorbaek, C. et al, "Divergent Functional Roles for p90rsk Kinase Domains", J. Biol. Chem., 270(32), 18848-18552 (1995).

Rouse, J. et al., A Novel Kinase Cascade Triggered by Stress and Heat Shock That Stimulates MAPKAP Kinase-2 and Phosphorylation of the Small Heat Shock Proteins, Cell, 78, 1027-1037 (1994).

Raingeaud, J. et al., "MMK3- and MMK6-Regulated Gene Expression Is Mediated by p38 Mitogen-Activated Protein Kinase Signal Transduction Pathway, Mol. Cell. Biol., 16, 1247-1255 (1996).

Chen, R.H. et al., "Phosphorylation of the c-Fos transrepression domain by mitogen-activated protein kinase and 90- kDa ribosomal S6 kinase", Proc. Natl. Acad. Sci. USA, 90, 10952-10956 (1993).

Moodie, S.A. et al., "Complexes of Ras-GTP with Raf-1 and Mitogen-Activated Protein Kinase Kinase", Science, 260 (5114), 1658-1661 (1993).

Frey, R.S. et al., "Involvement of Extracellular Signal-regulated Kinase 2 and Stress-activated Protein Kinase/Jun- NTerminal Kinase Activation by Transforming Growth Factor β in the Negative Growth Control of Breast Cancer Cells", Cancer Res., 57, 628-633 (1997).

Sivaraman, V.S., et al., "Hyperexpression of Mitogen-activated Protein Kinase in Human Breast Cancer", J. Clin. Invest., 99(7), 1478-1483 (1997).

Whelchel, A. et al., "Inhibition of ERK Activation Attenuates Endothelin-stimulated Airway Smooth Muscle Cell Proliferation", Am. J. Respir. Cell Mol. Biol., 16, 589-596 (1997).

Yuan, Z.Q. et al., "Frequent activation of AKT2 and induction of apoptosis by inhibition of phosphoinositide-3-OH kinase/Akt pathway in human ovarian cancer", Oncogene, 19, 2324-2330 (2000).

Kazuhiko, N. et al., "Akt/Protein Kinase B Prevents Injury-Induced Motoneuron Death and Accelerates Axonal Regeneration", J. of Neuroscience, 20(8), 2875-2986 (2000).

Molina, T.J. et al., "Profound block in thymocyte development in mice lacking p56lck", Nature, 357, 161-164 (1992).

Kimura, M. et al., "Cell Cycle-dependent Expression and Centrosome Localization of a Third Human Aurora/Ip11- related Protein Kinase, AIK3", J. Biol. Chem., 274(11), 13766-13771 (1997).

Douglas, G. et al., "Introduction to viral diseases", Cecil Textbook of Medicine, 20th Edition, vol. 2, p. 1739-1747, (1996).

Salomon, S. et al., "Cancer Chemotherapy", Lange Medical Book, Basic and Clinical Pharmacology, 7th edition, 55, p. 881-884 , (1998).

Torryiabe, K. et al., "Preparation of self-conaining arylthiazoles and insecticides", Chemical abstracts, [Columbus, Ohio, vol. 132, No. 8, 132: 93314o (2000).

IUPAC Compendium of Chemical Terminology on a definition of " aliphatic compounds" found from http://www.chemsoc.org/chembytes/goldbook/index.htm (last visited on Nov. 18, 2007).

International Search Report received in the corresponding PCT Application No. PCT/US2008/062329, (2008).

Alonso, M. et al., "GSK-3 Inhibitors: Discoveries and Developments", Current Medicinal Chemistry, 11, 755-763 (2004).

Anonymous, "Vertex Inhbitors of Aurora-2, glycogen synthase kinase-3 and Src Kinase", Expert Opin. Ther. Patents, 14(3): 439-443 (2004).

Baig, G.U. et al., "Triazines and Related Products. Part 28' Conversion of 3-Aryl-I-(2-cyanopheny1) triazenes into 3- Arylqu i nazol i n-4(3H) -ones with Formamide" J. Chem. Soc. Perkin Trans. I, 3765-2766 (1984).

Bischoff, J.R., et al., "A homologue of Drosophila aurora kinase is oncogenic and amplified in human colorectal cancers", The EMBO Journal, 17(11): 3052-3065 (1998).

Bischoff, J.R., et al., "The Aurora/lpl1p kinase family: regulators of chromosome segregation and cytokinesis", Cell Biology, 9, 454-459 (1999).

Brunswick, D.J. et al., "Cyclic Amidines. Part XXII. Novel Isomerism of Disubstituted Tricycioquinazolines and Molecular Orientations in Carcinogenesis", J. Chem. Soc. (C), 2641-2647 (1970).

Wolff, M.E., "Burger's Medicinal Chemistry and Drug Discovery," 5th ed., vol. 1: Principles and Practice, 975-977 (1995).

Cohen, P. et al., "The renaissance of GSK3," Nat. Rev. Mol. Biol., 2, 769-776 (2001).

Eldar-Finkelman, H. et al., "Challenges and opportunities with glycogen synthase kinase-3 inhibitors for insulin resistance and Type 2 diabetes treatment," Expert Opinion on Investigational Drugs, 12(9): 1511-1519 (2003).

Harrington, E.A. et al., "VX-680, a potent and selective small-molecule inhibitor of the Aurora kinases, suppresses tumor growth in vivo," Nat. Med., 10(3): 262-267 (2004).

Heutink, P., "Untangling tau-related dementia", Hum. Mol. Genet., 9(6): 979-986 (2000).

Nigg, E.A., "Mitotic Kinases as Regulators of Cell Division and its Checkpoints," Nat. Rev. Mol. Cell Biol., 2: 21-32 (2001).

Traxler, P. et al., "Use of a Pharmacophore Model for the Design of EGF-R Tyrosine Kinase Inhibitors: 4-(Phenylamino)pyrazolo[3,4-d]pyrimidines," J. Med. Chem., 40, 3601-3616 (1997).

Nakajima, Y. et al., "Pyrazoles agricultural and horticultural bactericides," CAPLUS listing Accession No. 1994:292136, JP 06065237 (1994).
Kelarev, V.I. et al., "Synthesis of amino derivatives of 1,3,5-triazine containing 1,3-4-thiadiazole fragments," Databaseca "Online!" Chemical Abstract Service, Columbus, OH, US; Database Accession No. 1998:69514 XP002242653 abstract & Izvestiya Vysshikh Uchebnkh Zavedenii, Khimiya I Khimicheskaya Tekhnologiya, 40(5): 27-32 (1997).
Chalmers, D.T. et al., "Corticotrophin-releasing factor receptors: from molecular biology to drug design," TiPS, 17, 769-776 (2001).
Kim, L. et al., "GSK3, a master switch regulating cell-fate specification and tumorigenesis," Current Opinion in Genetics & Development, 10:508-514 (2000).
Lyrer, P., Schweiz. Med. Woohen Schr., 124(45); 2005-2012 (1994).
Banker, G.S. et al., "Modern Pharmaceutics", 451 & 596, 3rd ed., Marcel Dekker, New York (1996).
Lovestone, S. et al., "Alzheimer's disease-like phosphorylation of the microtubule-associated protein tau by glycogen synthase kinase-3 in transfected mammalian cells", Curr. Biol., 4(12), 1077-86 (1994).
Ivashchenko A. V. et al., "Synethsis and Study of Heteroaromatic Ligands Containing a Pyrimidine Ring", Khim. Geterotsikl. Soedin., (12), 1673-7, (1980) (in English).
Brownlees, J. et al., "Tau phosphorylation in transgenic mice expressing glycogen synthase kinase-3beta transgenes", Neuroreport., 8(15), 3251-5 (1997).
Biagi, G. et al., "Synthesis of 4,6 Disubstituted and 4,5,6-Trisubstituted-2-Phenyl-pyrimidines and Their Affinity Towards A1 Adenosine Receptors", Farmaco., 52(1), 61-65 (1997).
Ali, N.M. et al, "Palladium-Catalyzed Cross Coupling Reactions of Arylboronic Acids with Pi-Deficient Heteroaryl Chlorides" Tetrahedron, 48 (37), 8117-8126 (1992).
Zhang, Z. et al., "Destabilization of β catenin by mutations in presenilin-1 potentiates neuronal apoptosis", Nature, 395, 698-702 (1998).
Takashima, K. et al., "Tau Protein Kinase I is Essential for Amyloid β-Protein-Induced Neurotoxicity", PNAS 90, 7789-7793 (1993).
Pei, J. et al., "Distribution, Levels, and Activity of Glycogen Synthase Kinase-3 in the Alzheimer Disease Brain", J. Neuropathol. Exp., 56, 70-78 (1997).
Rueeger, H et al., "Design, synthesis and SAR of a series of 2-substituted 4-amino-quinazoline neuropeptide Y Y5 receptor antagonists", Bioorg. Med. Chem. Lett., 10(11), 1175-1180 (2000).
Glossary of Class Names of Organic Compounds and Reactive Intermediates Based on Structure found from http://www.chem.qmul.ac.uk/iupac/class/index.html (last visited on Nov. 18, 2007).
Nomenclature found from http://www.cem.msu.edu/~reusch/VirtualText/nomen1.htm (last visited on Nov. 18, 2007).
Coghlan, M.P. et al., "Selective small molecule inhibitors of glycogen synthase kinase-3 modulate glycogen metabolism and gene transcription", Chemistry & Biology, 7, 793-83 (2000).
Klein, P.S. et al., "A molecular mechanism for the effect of lithium on development", PNAS, 93: 8455-8459 (1996).
Cross, D.A.E. et al., "The inhibition of glycogen synthase kinase-3 by insulin or insulin-like growth factor 1 in the rat skeletal muscle cell line L6 is blocked by wortmannin, but not by rapamycin: evidence that wortmannin blocks activation of the mitogen-activated protein kinase pathway in L6 cells between Ras and Raf", Biochem J., 303: 21-26 (1994).
Massillon, D. et al., "Identification of the glycogenic compound 5-iodotubercidin as a general protein kinase inhibitor", Biochem J., 299: 123-128 (1994).
Fox T. et al., "A single amino acid substitution makes ERK2 susceptible to pyridinyl imidazole inhibitors of p38 MAP kinase", Protein Sci., 7: 2249-2255 (1998).
Takayanagi, H. et al., "Suppression of arthritic bone destruction by adenovirus-mediated csk gene transfer to synoviocytes and osteoclasts", J. Clin. Invest., 104, 137-146 (1999).
Boschelli et al., "Small molecule inhibitors of Src family kinases", Drugs of the Future, 25(7): 717-736 (2000).
Talamonti, M.S. et al., "Increase in activity and level of pp60c-src in progressive stages of human colorectal cancer", J Clin Invest., 91(1): 53-60 (1993).
Lutz, M.L. et al., "Overexpression and Activation of the Tyrosine Kinase Src in Human Pancreatic Carcimona", Biochem. Biophys. Res. 243, 503-508 (1998).
Rosen, N. et al., "Analysis of pp60c-src Protein Kinase Activity in Human Tumor Cell Lines and Tissues", J.Biol. Chem., 261, 13754-13759 (1986).
Bolen, J.B. et al., "Activation of pp60c-src protein kinase activity in human colon carcinoma", PNAS, 84, 2251-2255 (1987).
Masaki, T. et al., "pp60c-src Activation in Hepatocellular Carcinoma of Humans and LEC Rats", Hapatology, 27, 1257 (1998).
Biscardi, J.S. et al., "c-Src, Receptor Tyrosine Kinases, and Human Cancer", Adv. Cancer Res., 76, 61 (1999).
Lynch, S.A. et al., "Increased Expression of the src Proto-Oncogene in Hairy Cell Leukemia and a Subgroup of B-Cell Lymphomas", Leukemia, 7(9), 1416-1422 (1993).
Wiener, J.R., "Decreased Src Tyrosine Kinase Activity Inhibits Malignant Human Ovarian Cancer Tumor Growth in a Nude Mouse Model", Clin. Cancer Res., 5, 2164-2170 (1999).
Staley, C.A. et al., "Decreased Tumorigenicity of a Human Colon Adenocarcinoma Cell Line by an Antisense Expression Vector Specific for c-Src", Cell Growth Diff., 8, 269-274 (1997).
Singhal, N. et al., "Synthesis and Antimalarial Activity of Some New Quinazoline Derivatives", Indian Chem. Soc., 61, 690-693 (1984).
Kim, Y.Z. et al., "Synthesis and Antimicrobial Activity of Novel [(3-Aminopyrimidiniumyl)thio]methyl Cephalosporins", J. Med. Chem., 37(22); 3828-3833 (1994).
Namikowa et al., "Akt/Protein Kinase B Prevents Injury-Induced Motoneuron Death and Accelerates Axonal Regeneration", The Journal of Neuroscience, Apr. 15, 2000, 20(8):2875-2886.

* cited by examiner

AMINOPYRIMIDINES USEFUL AS KINASE INHIBITORS

This application is a continuation application of International Patent Application No. PCT/US2008/062329, filed on May 2, 2008, which in turn claims the benefit under 35 U.S.C. §119, of U.S. Provisional patent application No. 60/915,575, filed May 2, 2007, entitled "AMINOPYRIMIDINES USEFUL AS KINASE INHIBITORS", and the entire contents of these applications are hereby incorporated by reference.

TECHNICAL FIELD OF THE INVENTION

The present invention relates to compounds useful as inhibitors of Aurora protein kinases. The invention also relates to pharmaceutically acceptable compositions comprising the compounds of the invention, methods of using the compounds and compositions in the treatment of various disorders, and processes for preparing the compounds.

BACKGROUND OF THE INVENTION

The Aurora proteins are a family of three related serine/threonine kinases (termed Aurora-A, -B and -C) that are essential for progression through the mitotic phase of cell cycle. Specifically Aurora-A plays a crucial role in centrosome maturation and segregation, formation of the mitotic spindle and faithful segregation of chromosomes. Aurora-B is a chromosomal passenger protein that plays a central role in regulating the alignment of chromosomes on the meta-phase plate, the spindle assembly checkpoint and for the correct completion of cytokinesis.

Overexpression of Aurora-A, -B or -C has been observed in a range of human cancers including colorectal, ovarian, gastric and invasive duct adenocarcinomas.

A number of studies have now demonstrated that depletion or inhibition of Aurora-A or -B in human cancer cell lines by siRNA, dominant negative antibodies or neutralizing antibodies disrupts progression through mitosis with accumulation of cells with 4N DNA, and in some cases this is followed by endoreduplication and cell death.

The Aurora kinases are attractive targets due to their association with numerous human cancers and the roles they play in the proliferation of these cancer cells. Accordingly, there is a need for compounds that inhibit Aurora kinases.

SUMMARY OF THE INVENTION

This invention provides compounds and pharmaceutically acceptable compositions thereof that are useful as inhibitors of Aurora protein kinases. These compounds are represented by formula I:

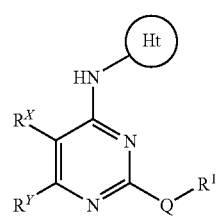

or a pharmaceutically acceptable salt thereof, wherein the variables are as defined herein.

These compounds and pharmaceutically acceptable compositions thereof are useful for inhibiting kinases in vitro, in vivo, and ex vivo. Such uses include treating or preventing myeloproliferative disorders and proliferative disorders such as melanoma, myeloma, leukemia, lymphoma, neuroblastoma, and cancer. Other uses include the study of kinases in biological and pathological phenomena; the study of intracellular signal transduction pathways mediated by such kinases; and the comparative evaluation of new kinase inhibitors.

DETAILED DESCRIPTION OF THE INVENTION

One embodiment of this invention provides a compound of formula I:

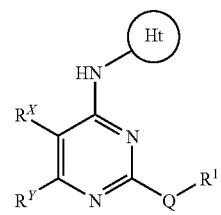

or a pharmaceutically acceptable salt thereof, wherein:
Ht is

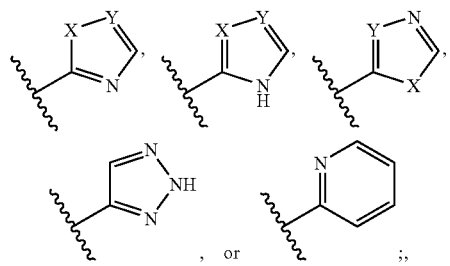

wherein
said Ht is optionally and independently substituted with $R^2$ and $R^{2'}$;
X is CH, N, O, or S;
Y is CH, N, O, or S;
Q is —O—, —NR'—, —S—, —C(=O)—, or —C(R')$_2$—;
$R^X$ is H or F;
$R^Y$ is —Z—$R^{10}$;
$R^1$ is T-(Ring D);
Ring D is a 5-7 membered monocyclic aryl or heteroaryl ring, wherein said heteroaryl has 1-4 ring heteroatoms selected from O, N, and S; Ring D can optionally be fused with Ring D';
Ring D' is a 5-8 aromatic, partially saturated, or fully unsaturated ring containing 0-4 ring heteroatoms selected from nitrogen, oxygen or sulfur;
Ring D and Ring D' are each independently and optionally substituted with 0-4 occurrences of oxo or —W—$R^5$;
each T is independently a $C_{1-4}$ alkylidene chain or is absent;
$R^2$ is H, $C_{1-3}$ alkyl, or cyclopropyl;
$R^{2'}$ is H;
each Z and W is independently absent or a $C_{1-10}$ alkylidene chain wherein up to six methylene units of the alkylidene chain are optionally replaced by V;

each V is selected from —O—, —C(=O)—, —S(O)—, —S(O)$_2$—, —S—, or —N(R$^4$)—;

each R$^5$ is independently —R, -halo, —OR, —C(=O)R, —CO$_2$R, —COCOR, COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$ (C$_{1-6}$ aliphatic), —N(R$^4$)N(R$^4$)$_2$, —C=NN(R$^4$)$_2$, —C=N—OR, —N(R$^7$)CON(R$^7$)$_2$, —N(R$^7$)SO$_2$N(R$^7$)$_2$, —N(R$^4$)SO$_2$R, or —OC(=O)N(R$^7$)$_2$;

each R is H, a C$_{1-6}$ aliphatic group, a C$_{6-10}$ aryl ring, a heteroaryl ring having 5-10 ring atoms, or a heterocyclyl ring having 4-10 ring atoms; wherein said heteroaryl or heterocyclyl ring has 1-4 ring heteroatoms selected from nitrogen, oxygen, or sulfur; R is optionally substituted with 0-6 R$^9$;

each R$^4$ is —R$^7$, —COR$^7$, —CO$_2$R$^7$, —CON(R$^7$)$_2$, or —SO$_2$R$^7$;

each R$^7$ is independently H or an optionally substituted C$_{1-6}$ aliphatic group; or two R$^7$ on the same nitrogen are taken together with the nitrogen to form an optionally substituted 4-8 membered heterocyclyl or heteroaryl ring containing 1-4 heteroatoms selected from nitrogen, oxygen, or sulfur;

each R$^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N(R')$_2$, —OC(=O)R', —N(R')COR', —N(R')CO$_2$ (C$_{1-6}$ aliphatic), —N(R')N(R')$_2$, —N(R')CON(R')$_2$, —N(R')SO$_2$N(R')$_2$, —N(R')SO$_2$R', —OC(=O)N(R')$_2$, =NN(R')$_2$, =N—OR', or =O;

each R$^{10}$ is a 4-membered heterocyclic ring containing 1 heteroatom selected from O, N, and S; each R$^{10}$ is optionally substituted with 0-6 occurrences of J;

each J is independently R, -halo, —OR, oxo, —C(=O)R, —CO$_2$R, —COLOR, —COCH$_2$COR, —NO$_2$, —CN, —S(O)R, —S(O)$_2$R, —SR, —N(R$^4$)$_2$, —CON(R$^7$)$_2$, —SO$_2$N(R$^7$)$_2$, —OC(=O)R, —N(R$^7$)COR, —N(R$^7$)CO$_2$ (C$_{1-6}$ aliphatic), —N(R$^4$)N(R$^4$)$_2$, =NN(R$^4$)$_2$, =N—OR, —N(R$^7$)CON(R$^7$)$_2$, —N(R$^7$)SO$_2$N(R$^7$)$_2$, —N(R$^4$)SO$_2$R, —OC(=O)N(R$^7$)$_2$, or —OP(=O) (OR")$_2$; or 2 J groups, on the same atom or on different atoms, together with the atom(s) to which they are bound, form a 3-8 membered saturated, partially saturated, or unsaturated ring having 0-2 heteroatoms selected from O, N, or S; wherein 1-4 hydrogen atoms on the ring formed by the 2 J groups is optionally replaced with halo, C$_{1-3}$alkyl, or —O(C$_{1-3}$alkyl); or two hydrogen atoms on the ring are optionally replaced with oxo or a spiro-attached C$_{3-4}$ cycloalkyl; wherein said C$_{1-3}$alkyl is optionally substituted with 1-3 fluorine;

each R' is independently H or a C$_{1-6}$ aliphatic group; or two R', together with atom(s) to which they are bound, form a 3-6 membered carbocyclyl or a 3-6 membered heterocyclyl containing 0-1 heteroatoms selected from O, N, and S; and each R" is independently H or C$_{1-2}$alkyl.

In one embodiment, Ht

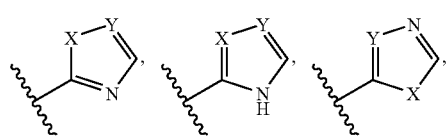

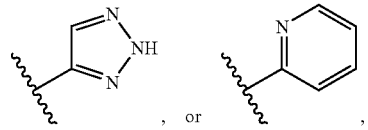

wherein said Ht is optionally and independently substituted with R$^2$ and R$^{2'}$, provided that Ht is not pyrazolyl or thiazolyl.

In one embodiment, Ht is selected from the following:

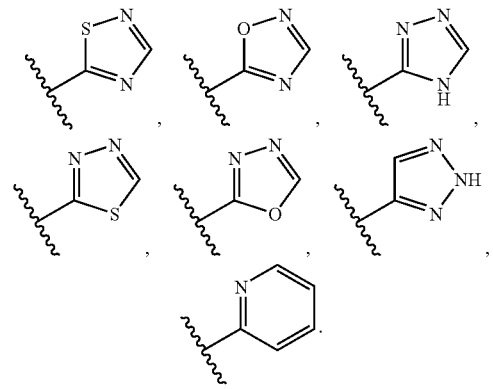

In some embodiments, Ht is

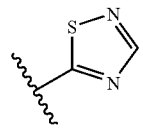

In some embodiments, Ht is

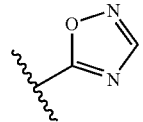

In some embodiments, Ht is

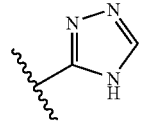

In some embodiments, Ht is

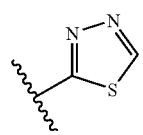

In some embodiments, Ht is

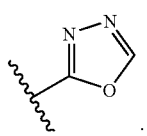 [SMILES: *c1nnco1]

In some embodiments, Ht is

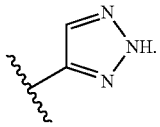 [SMILES: *c1cn[nH]n1]

In some embodiments, Ht is

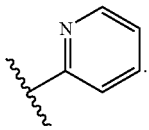 [SMILES: *c1ccccn1]

In some embodiments Q is S. In other embodiments, Q is O.

In some embodiments, R² is attached at the meta position and R²' is attached at the ortho position of the Het ring. Examples of Ht groups which such attachments are shown below:

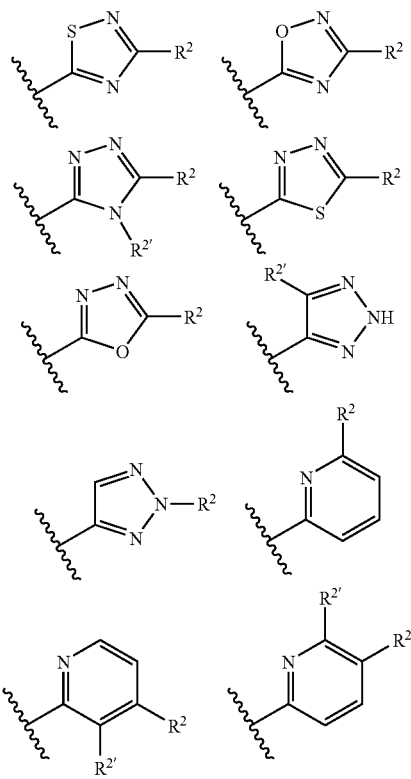

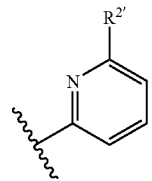

In some embodiments, $R^2$ is H or $C_{1-3}$ alkyl.

In another embodiment, Ring D is a 5-6 membered monocyclic aryl or heteroaryl ring. In some embodiments, Ring D is fused with Ring D'.

In one aspect of the invention, Ring D-D' is an 8-12 membered bicyclic aryl or heteroaryl containing 1-5 heteroatoms selected from nitrogen, oxygen, or sulfur. In some embodiments, Ring D-D' is a 6:6 ring system. In some embodiments, Ring D-D' is quinoline. In other embodiments, Ring D-D' is a 6:5 ring system. In some embodiments, said 6:5 ring system contains 2 nitrogen atoms. In some embodiments, Ring D-D' is a benzimidazole, indazole, or imidazopyridine ring. In other embodiments, Ring D-D' is a benzimidazole ring.

In another aspect of the invention, Ring D is a 5-6 membered monocyclic aryl or heteroaryl ring; and wherein D is not fused with D'. In some embodiments, Ring D is phenyl. In one embodiment, Ring D is phenyl where the phenyl is independently substituted with one or two substituents selected from -halo and —N(R⁷)CO₂(C₁₋₆ aliphatic). In another embodiment, Ring D is phenyl where the phenyl is independently substituted with —F and —NHCO₂(C₁₋₃ aliphatic). In yet another embodiment, Ring D is phenyl, where the phenyl is independently substituted with —F and —NHCO₂(cyclopropyl). In one embodiment, Ring D is

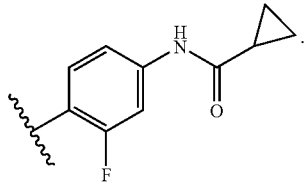 [SMILES: *c1ccc(NC(=O)C2CC2)cc1F]

In some embodiments, T is absent.

In another aspect of the invention, $R^Y$ is —Z—$R^{10}$.

In another embodiment, Z is absent. In yet another embodiment, Z is a $C_{1-6}$ alkylidene chain wherein 1-2 methylene units of Z is optionally replaced by O, —N(R⁴)—, or S. In some embodiments, Z is a $C_{1-4}$ alkylidene chain.

In another aspect of this invention, $R^{10}$ is an optionally substituted azetidine. In some embodiments, $R^Y$ is represented by formula i:

i

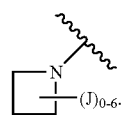

In other embodiments, $R^Y$ is represented by formula ii-a:

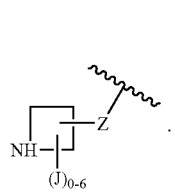

Another embodiment provides the following compound of Table 1:

TABLE 1

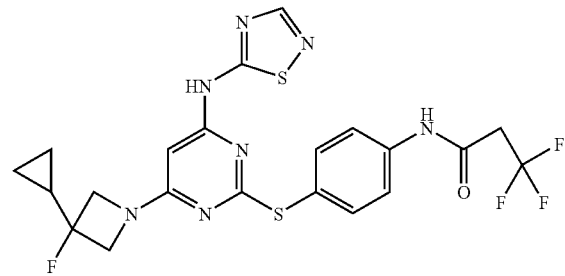 [SMILES: O=C(CC(F)(F)F)Nc1ccc(Sc2nc(Nc3ncns3)cc(N3CC(F)(C4CC4)C3)n2)cc1]

I-1

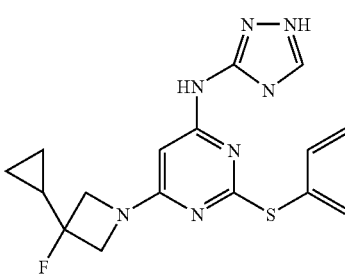

I-2

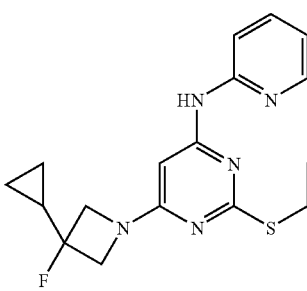

I-3

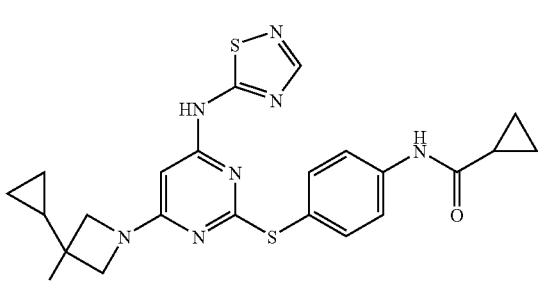

I-4

TABLE 1-continued

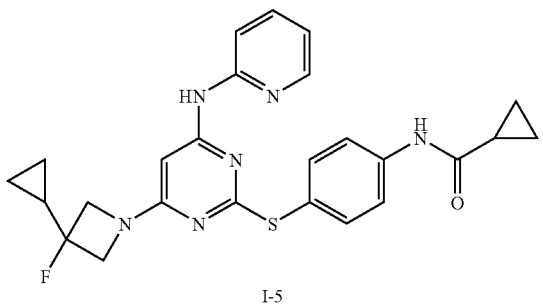

I-5

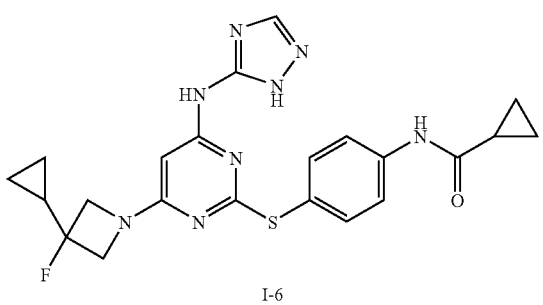

I-6

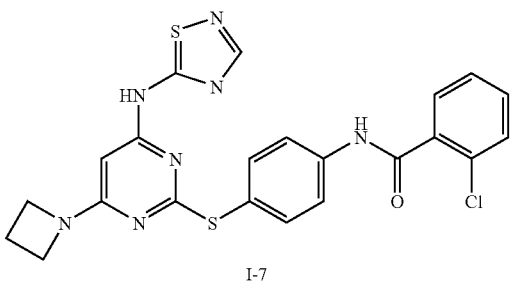

I-7

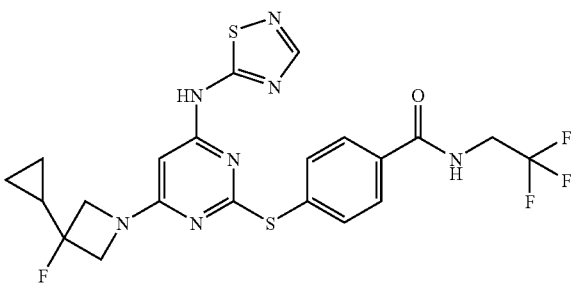 [SMILES: O=C(NCC(F)(F)F)c1ccc(Sc2nc(Nc3ncns3)cc(N3CC(F)(C4CC4)C3)n2)cc1]

I-8

For purposes of this invention, the chemical elements are identified in accordance with the Periodic Table of the Elements, CAS version, Handbook of Chemistry and Physics, 75th Ed. Additionally, general principles of organic chemistry are described in texts known to those of ordinary skill in the art, including, for example, "Organic Chemistry", Thomas Sorrell, University Science Books, Sausalito: 1999, and "March's Advanced Organic Chemistry", $5^{th}$ Ed., Ed.: Smith, M. B. and March, J., John Wiley & Sons, New York: 2001, the entire contents of which are hereby incorporated by reference.

As described herein, a specified number range of atoms includes any integer therein. For example, a group having from 1-4 atoms could have 1, 2, 3, or 4 atoms.

As described herein, compounds of the invention may optionally be substituted with one or more substituents, such as are illustrated generally above, or as exemplified by particular classes, subclasses, and species of the invention. It will be appreciated that the phrase "optionally substituted" is used interchangeably with the phrase "substituted or unsubstituted." In general, the term "substituted", whether preceded by the term "optionally" or not, refers to the replacement of hydrogen radicals in a given structure with the radical of a specified substituent. Unless otherwise indicated, an optionally substituted group may have a substituent at each substitutable position of the group, and when more than one position in any given structure may be substituted with more than one substituent selected from a specified group, the substituent may be either the same or different at every position. Combinations of substituents envisioned by this invention are preferably those that result in the formation of stable or chemically feasible compounds.

The term "stable", as used herein, refers to compounds that are not substantially altered when subjected to conditions to allow for their production, detection, and preferably their recovery, purification, and use for one or more of the purposes disclosed herein. In some embodiments, a stable compound or chemically feasible compound is one that is not substantially altered when kept at a temperature of 40° C. or less, in the absence of moisture or other chemically reactive conditions, for at least a week.

The term "aliphatic" or "aliphatic group", and the like, as used herein, means an unbranched or branched, straight-chain or cyclic, substituted or unsubstituted hydrocarbon that is completely saturated or that contains one or more units of unsaturation that has a single point of attachment to the rest of the molecule. Suitable aliphatic groups include, but are not limited to, linear or branched, substituted or unsubstituted alkyl, alkenyl, or alkynyl groups. Specific examples include, but are not limited to, methyl, ethyl, isopropyl, n-propyl, sec-butyl, vinyl, n-butenyl, ethynyl, and tert-butyl.

The term "cycloaliphatic" (or "carbocycle" or "carbocyclyl" or "cycloalkyl" and the like) refers to a monocyclic $C_3$-$C_8$ hydrocarbon or bicyclic $C_8$-$C_{12}$ hydrocarbon that is completely saturated or that contains one or more units of unsaturation, but which is not aromatic, that has a single point of attachment to the rest of the molecule wherein any individual ring in said bicyclic ring system has 3-7 members. Suitable cycloaliphatic groups include, but are not limited to, cycloalkyl and cycloalkenyl groups. Specific examples include, but are not limited to, cyclohexyl, cyclopropenyl, and cyclobutyl.

The term "alkyl" as used herein, means an unbranched or branched, straight-chain hydrocarbon that is completely saturated and has a single point of attachment to the rest of the molecule. Specific examples of alkyl groups include, but are not limited to, methyl, ethyl, isopropyl, n-propyl, and sec-butyl.

The term "cycloalkyl" refers to a monocyclic hydrocarbon that is completely saturated and has a single point of attachment to the rest of the molecule. Suitable cycloalkyl groups include, but are not limited to, cyclopropyl, cyclobutyl, and cyclopentyl.

In the compounds of this invention, rings include linearly-fused, bridged, or spirocyclic rings. Examples of bridged cycloaliphatic groups include, but are not limited to, bicyclo[3.3.2]decane, bicyclo[3.1.1]heptane, and bicyclo[3.2.2]nonane.

The term "heterocycle", "heterocyclyl", or "heterocyclic", and the like, as used herein means non-aromatic, monocyclic or bicyclic ring in which one or more ring members are an independently selected heteroatom. In some embodiments, the "heterocycle", "heterocyclyl", or "heterocyclic" group has three to ten ring members in which one or more ring members is a heteroatom independently selected from oxygen, sulfur, nitrogen, or phosphorus, and each ring in the system contains 3 to 7 ring members. Examples of bridged heterocycles include, but are not limited to, 7-aza-bicyclo[2.2.1]heptane and 3-aza-bicyclo[3.2.2]nonane.

Suitable heterocycles include, but are not limited to, 3-1H-benzimidazol-2-one, 3-(1-alkyl)-benzimidazol-2-one, 2-tetrahydrofuranyl, 3-tetrahydrofuranyl, 2-tetrahydrothiophenyl, 3-tetrahydrothiophenyl, 2-morpholino, 3-morpholino, 4-morpholino, 2-thiomorpholino, 3-thiomorpholino, 4-thiomorpholino, 1-pyrrolidinyl, 2-pyrrolidinyl, 3-pyrrolidinyl, 1-tetrahydropiperazinyl, 2-tetrahydropiperazinyl, 3-tetrahydropiperazinyl, 1-piperidinyl, 2-piperidinyl, 3-piperidinyl, 1-pyrazolinyl, 3-pyrazolinyl, 4-pyrazolinyl, 5-pyrazolinyl, 1-piperidinyl, 2-piperidinyl, 3-piperidinyl, 4-piperidinyl, 2-thiazolidinyl, 3-thiazolidinyl, 4-thiazolidinyl, 1-imidazolidinyl, 2-imidazolidinyl, 4-imidazolidinyl, 5-imidazolidinyl, indolinyl, tetrahydroquinolinyl, tetrahydroisoquinolinyl, benzothiolane, benzodithiane, and 1,3-dihydro-imidazol-2-one.

As used herein, the term "Ht" is interchangeable with "Het" and

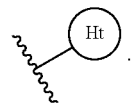

The term "heteroatom" means one or more of oxygen, sulfur, nitrogen, phosphorus, or silicon (including, any oxidized form of nitrogen, sulfur, phosphorus, or silicon; the quaternized form of any basic nitrogen or; a substitutable nitrogen of a heterocyclic ring, for example N (as in 3,4-dihydro-2H-pyrrolyl), NH (as in pyrrolidinyl) or $NR^+$ (as in N-substituted pyrrolidinyl)).

The term "aryl" refers to monocyclic, or bicyclic ring having a total of five to twelve ring members, wherein at least one ring in the system is aromatic and wherein each ring in the system contains 3 to 7 ring members. The term "aryl" may be used interchangeably with the term "aryl ring". The term "aryl" also refers to heteroaryl ring systems as defined hereinbelow.

The term "heteroaryl", refers to monocyclic or bicyclic ring having a total of five to twelve ring members, wherein at least one ring in the system is aromatic, at least one ring in the system contains one or more heteroatoms, and wherein each ring in the system contains 3 to 7 ring members. The term "heteroaryl" may be used interchangeably with the term "heteroaryl ring" or the term "heteroaromatic". Suitable heteroaryl rings include, but are not limited to, 2-furanyl, 3-furanyl, N-imidazolyl, 2-imidazolyl, 4-imidazolyl, 5-imidazolyl, benzimidazolyl, 3-isoxazolyl, 4-isoxazolyl, 5-isoxazolyl, 2-oxazolyl, 4-oxazolyl, 5-oxazolyl, N-pyrrolyl, 2-pyrrolyl, 3-pyrrolyl, 2-pyridyl, 3-pyridyl, 4-pyridyl, 2-pyrimidinyl, 4-pyrimidinyl, 5-pyrimidinyl, pyridazinyl (e.g., 3-pyridazinyl), 2-thiazolyl, 4-thiazolyl, 5-thiazolyl, tetrazolyl (e.g., 5-tetrazolyl), triazolyl (e.g., 2-triazolyl and 5-triazolyl), 2-thienyl, 3-thienyl, benzofuryl, benzothiophenyl, indolyl (e.g., 2-indolyl), pyrazolyl (e.g., 2-pyrazolyl), isothiazolyl, 1,2,3-oxadiazolyl, 1,2,5-oxadiazolyl, 1,2,4-oxadiazolyl, 1,2,3-triazolyl, 1,2,3-thiadiazol $C_3$-$C_8$ yl, 1,3,4-thiadiazolyl, 1,2,5-thiadiazolyl, purinyl, pyrazinyl, 1,3,5-triazinyl, quinolinyl (e.g., 2-quinolinyl, 3-quinolinyl, 4-quinolinyl), and isoquinolinyl (e.g., 1-isoquinolinyl, 3-isoquinolinyl, or 4-isoquinolinyl).

The term "unsaturated", as used herein, means that a moiety has one or more units of unsaturation.

The term "halogen" means F, Cl, Br, or I.

The term "protecting group", as used herein, refers to an agent used to temporarily block one or more desired reactive sites in a multifunctional compound. In certain embodiments, a protecting group has one or more, or preferably all, of the following characteristics: a) reacts selectively in good yield to give a protected substrate that is stable to the reactions occurring at one or more of the other reactive sites; and b) is selectively removable in good yield by reagents that do not attack the regenerated functional group. Exemplary protecting groups are detailed in Greene, T. W., Wuts, P. G in "Protective Groups in Organic Synthesis", Third Edition, John Wiley & Sons, New York: 1999, and other editions of this book, the entire contents of which are hereby incorporated by reference. The term "nitrogen protecting group", as used herein, refers to an agents used to temporarily block one or more desired nitrogen reactive sites in a multifunctional compound. Preferred nitrogen protecting groups also possess the characteristics exemplified above, and certain exemplary nitrogen protecting groups are also detailed in Chapter 7 in Greene, T. W., Wuts, P. G in "Protective Groups in Organic Synthesis", Third Edition, John Wiley & Sons, New York: 1999, the entire contents of which are hereby incorporated by reference.

Unless otherwise indicated, structures depicted herein are also meant to include all isomeric (e.g., enantiomeric, diastereomeric, and geometric (or conformational)) forms of the structure; for example, the R and S configurations for each asymmetric center, (Z) and (E) double bond isomers, and (Z) and (E) conformational isomers. Therefore, single stereochemical isomers as well as enantiomeric, diastereomeric, and geometric (or conformational) mixtures of the present compounds are within the scope of the invention.

Unless otherwise indicated, all tautomeric forms of the compounds of the invention are within the scope of the invention. Unless otherwise indicated, a substituent can freely rotate around any rotatable bonds. For example, a substituent drawn as

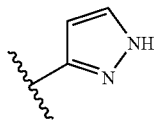

also represents

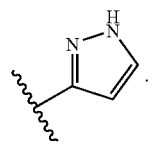

Likewise, a substituent drawn as

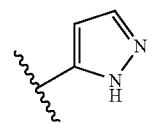

also represents

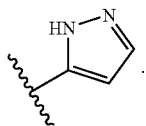 [SMILES: *c1ccn[nH]1]

Additionally, unless otherwise indicated, structures depicted herein are also meant to include compounds that differ only in the presence of one or more isotopically enriched atoms. For example, compounds having the present structures except for the replacement of hydrogen by deuterium or tritium, or the replacement of a carbon by a $^{13}$C- or $^{14}$C-enriched carbon are within the scope of this invention. Such compounds are useful, for example, as analytical tools or probes in biological assays.

The compounds of this invention may be prepared in light of the specification using steps generally known to those of ordinary skill in the art. Those compounds may be analyzed by known methods, including but not limited to LCMS (liquid chromatography mass spectrometry) and NMR (nuclear magnetic resonance). It should be understood that the specific conditions shown below are only examples, and are not meant to limit the scope of the conditions that can be used for making compounds of this invention. Instead, this invention also includes conditions that would be apparent to those skilled in that art in light of this specification for making the compounds of this invention. Unless otherwise indicated, all variables in the following schemes are as defined herein.

The following abbreviations are used:

HPLC is high performance liquid chromatography

LCMS liquid chromatography mass spectrometry $^1$H NMR is nuclear magnetic resonance

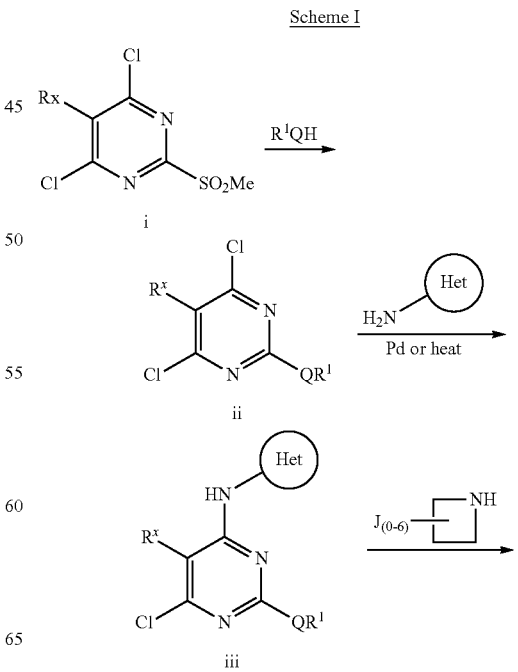

Scheme I

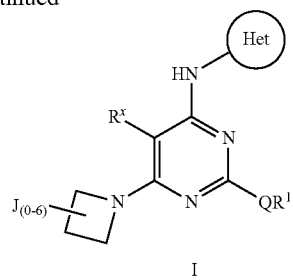

I

Scheme I above shows a generic method for making compounds of this invention. Dichloropyridine i is combined with HQ-R$^1$ to form intermediate ii, which, upon treatment with either Pd or heat and the aminoheteroaryl, forms aminopyrimidine iii. Aminopyrimidine iii is combined with the azetidine to form compounds of formula I.

Additionally, the compounds of this invention may be prepared according to the methods shown in U.S. Pat. Nos. 6,846,928, 7,179,826, 7,179,826, and United States Patent Publication 2004/0009981.

Accordingly, this invention relates to processes for making the compounds of this invention.

Methods for evaluating the activity of the compounds of this invention (e.g., kinase assays) are known in the art and are also described in the examples set forth.

The activity of the compounds as protein kinase inhibitors may be assayed in vitro, in vivo or in a cell line. In vitro assays include assays that determine inhibition of either the kinase activity or ATPase activity of the activated kinase. Alternate in vitro assays quantitate the ability of the inhibitor to bind to the protein kinase and may be measured either by radiolabelling the inhibitor prior to binding, isolating the inhibitor/kinase complex and determining the amount of radiolabel bound, or by running a competition experiment where new inhibitors are incubated with the kinase bound to known radioligands.

Another aspect of the invention relates to inhibiting kinase activity in a biological sample, which method comprises contacting said biological sample with a compound of formula I or a composition comprising said compound. The term "biological sample", as used herein, means an in vitro or an ex vivo sample, including, without limitation, cell cultures or extracts thereof; biopsied material obtained from a mammal or extracts thereof; and blood, saliva, urine, feces, semen, tears, or other body fluids or extracts thereof.

Inhibition of kinase activity in a biological sample is useful for a variety of purposes that are known to one of skill in the art. Examples of such purposes include, but are not limited to, blood transfusion, organ-transplantation, biological specimen storage, and biological assays.

Inhibition of kinase activity in a biological sample is also useful for the study of kinases in biological and pathological phenomena; the study of intracellular signal transduction pathways mediated by such kinases; and the comparative evaluation of new kinase inhibitors.

The Aurora protein kinase inhibitors or pharmaceutical salts thereof may be formulated into pharmaceutical compositions for administration to animals or humans. These pharmaceutical compositions, which comprise an amount of the Aurora protein inhibitor effective to treat or prevent an Aurora-mediated condition and a pharmaceutically acceptable carrier, are another embodiment of the present invention.

The term "Aurora-mediated condition" or "Aurora-mediated disease" as used herein means any disease or other deleterious condition in which Aurora (Aurora A, Aurora B, and Aurora C) is known to play a role. Such conditions include, without limitation, cancer, proliferative disorders, and myeloproliferative disorders.

Examples of myeloproliferative disorders include, but are not limited to, polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

The term "cancer" also includes, but is not limited to, the following cancers: epidermoid Oral: buccal cavity, lip, tongue, mouth, pharynx; Cardiac: sarcoma (angiosarcoma, fibrosarcoma, rhabdomyosarcoma, liposarcoma), myxoma, rhabdomyoma, fibroma, lipoma and teratoma; Lung: bronchogenic carcinoma (squamous cell or epidermoid, undifferentiated small cell, undifferentiated large cell, adenocarcinoma), alveolar (bronchiolar) carcinoma, bronchial adenoma, sarcoma, lymphoma, chondromatous hamartoma, mesothelioma; Gastrointestinal: esophagus (squamous cell carcinoma, larynx, adenocarcinoma, leiomyosarcoma, lymphoma), stomach (carcinoma, lymphoma, leiomyosarcoma), pancreas (ductal adenocarcinoma, insulinoma, glucagonoma, gastrinoma, carcinoid tumors, vipoma), small bowel or small intestines (adenocarcinoma, lymphoma, carcinoid tumors, Karposi's sarcoma, leiomyoma, hemangioma, lipoma, neurofibroma, fibroma), large bowel or large intestines (adenocarcinoma, tubular adenoma, villous adenoma, hamartoma, leiomyoma), colon, colon-rectum, colorectal; rectum, Genitourinary tract: kidney (adenocarcinoma, Wilm's tumor [nephroblastoma], lymphoma, leukemia), bladder and urethra (squamous cell carcinoma, transitional cell carcinoma, adenocarcinoma), prostate (adenocarcinoma, sarcoma), testis (seminoma, teratoma, embryonal carcinoma, teratocarcinoma, choriocarcinoma, sarcoma, interstitial cell carcinoma, fibroma, fibroadenoma, adenomatoid tumors, lipoma); Liver: hepatoma (hepatocellular carcinoma), cholangiocarcinoma, hepatoblastoma, angiosarcoma, hepatocellular adenoma, hemangioma, biliary passages; Bone: osteogenic sarcoma (osteosarcoma), fibrosarcoma, malignant fibrous histiocytoma, chondrosarcoma, Ewing's sarcoma, malignant lymphoma (reticulum cell sarcoma), multiple myeloma, malignant giant cell tumor chordoma, osteochronfroma (osteocartilaginous exostoses), benign chondroma, chondroblastoma, chondromyxofibroma, osteoid osteoma and giant cell tumors; Nervous system: skull (osteoma, hemangioma, granuloma, xanthoma, osteitis deformans), meninges (meningioma, meningiosarcoma, gliomatosis), brain (astrocytoma, medulloblastoma, glioma, ependymoma, germinoma [pinealoma], glioblastoma multiform, oligodendroglioma, schwannoma, retinoblastoma, congenital tumors), spinal cord neurofibroma, meningioma, glioma, sarcoma); Gynecological: uterus (endometrial carcinoma), cervix (cervical carcinoma, pre-tumor cervical dysplasia), ovaries (ovarian carcinoma [serous cystadenocarcinoma, mucinous cystadenocarcinoma, unclassified carcinoma], granulosa-thecal cell tumors, Sertoli-Leydig cell tumors, dysgerminoma, malignant teratoma), vulva (squamous cell carcinoma, intraepithelial carcinoma, adenocarcinoma, fibrosarcoma, melanoma), vagina (clear cell carcinoma, squamous cell carcinoma, botryoid sarcoma (embryonal rhabdomyosarcoma), fallopian tubes (carcinoma), breast; Hematologic: blood (myeloid leukemia [acute and chronic], acute lymphoblastic leukemia, chronic lymphocytic leukemia, myeloproliferative diseases, multiple myeloma, myelodysplastic syndrome), Hodgkin's disease, non-Hodgkin's lymphoma [malignant lymphoma] hairy cell; lymphoid disorders; Skin: malignant melanoma, basal cell carcinoma, squamous cell carcinoma, Karposi's sarcoma, keratoacanthoma, moles dysplastic nevi, lipoma, angioma, dermatofibroma, keloids, psoriasis, Thyroid gland: papillary thyroid carcinoma, follicular thyroid carcinoma; medullary thyroid carcinoma, undifferentiated thyroid cancer, multiple endocrine neoplasia type 2A, multiple endocrine neoplasia type 2B, familial medullary thyroid cancer, pheochromocytoma, paraganglioma; and Adrenal glands: neuroblastoma. Thus, the term "cancerous cell" as provided herein, includes a cell afflicted by any one of the above-identified conditions. In some embodiments, the cancer is selected from colorectal, thyroid, or breast cancer.

In some embodiments, the compounds of this invention are useful for treating cancer, such as colorectal, thyroid, breast, and lung cancer; and myeloproliferative disorders, such as polycythemia vera, thrombocythemia, myeloid metaplasia with myelofibrosis, chronic myelogenous leukemia, chronic myelomonocytic leukemia, hypereosinophilic syndrome, juvenile myelomonocytic leukemia, and systemic mast cell disease.

In some embodiments, the compounds of this invention are useful for treating hematopoietic disorders, in particular, acute-myelogenous leukemia (AML), chronic-myelogenous leukemia (CML), acute-promyelocytic leukemia (APL), and acute lymphocytic leukemia (ALL).

In addition to the compounds of this invention, pharmaceutically acceptable derivatives or prodrugs of the compounds of this invention may also be employed in compositions to treat or prevent the above-identified disorders.

A "pharmaceutically acceptable derivative or prodrug" means any pharmaceutically acceptable ester, salt of an ester or other derivative of a compound of this invention which, upon administration to a recipient, is capable of providing, either directly or indirectly, a compound of this invention or an inhibitorily active metabolite or residue thereof. Such derivatives or prodrugs include those that increase the bioavailability of the compounds of this invention when such compounds are administered to a patient (e.g., by allowing an orally administered compound to be more readily absorbed into the blood) or which enhance delivery of the parent compound to a biological compartment (e.g., the brain or lymphatic system) relative to the parent species.

Examples of pharmaceutically acceptable prodrugs of the compounds of this invention include, without limitation, esters, amino acid esters, phosphate esters, metal salts and sulfonate esters.

The compounds of this invention can exist in free form for treatment, or where appropriate, as a pharmaceutically acceptable salt.

As used herein, the term "pharmaceutically acceptable salt" refers to salts of a compound which are, within the scope of sound medical judgment, suitable for use in contact with the tissues of humans and lower animals without undue toxicity, irritation, allergic response and the like, and are commensurate with a reasonable benefit/risk ratio.

Pharmaceutically acceptable salts of the compounds of this invention include those derived from suitable inorganic and organic acids and bases. These salts can be prepared in situ during the final isolation and purification of the compounds. Acid addition salts can be prepared by 1) reacting the purified compound in its free-based form with a suitable organic or inorganic acid and 2) isolating the salt thus formed.

Examples of suitable acid salts include acetate, adipate, alginate, aspartate, benzoate, benzenesulfonate, bisulfate, butyrate, citrate, camphorate, camphorsulfonate, cyclopentanepropionate, digluconate, dodecylsulfate, ethanesulfonate, formate, fumarate, glucoheptanoate, glycerophosphate, glycolate, hemisulfate, heptanoate, hexanoate, hydrochloride, hydrobromide, hydroiodide, 2-hydroxyethanesulfonate, lactate, maleate, malonate, methanesulfonate, 2-naphthalenesulfonate, nicotinate, nitrate, oxalate, palmoate, pectinate, persulfate, 3-phenylpropionate, phosphate, picrate, pivalate, propionate, salicylate, succinate, sulfate, tartrate, thiocyanate, tosylate and undecanoate. Other acids, such as oxalic, while not in themselves pharmaceutically acceptable, may be employed in the preparation of salts useful as intermediates in obtaining the compounds of the invention and their pharmaceutically acceptable acid addition salts.

Base addition salts can be prepared by 1) reacting the purified compound in its acid form with a suitable organic or inorganic base and 2) isolating the salt thus formed.

Salts derived from appropriate bases include alkali metal (e.g., sodium and potassium), alkaline earth metal (e.g., magnesium), ammonium and $N^+(C_{1-4} alkyl)_4$ salts. This invention also envisions the quaternization of any basic nitrogen-containing groups of the compounds disclosed herein. Water or oil-soluble or dispersible products may be obtained by such quaternization.

Base addition salts also include alkali or alkaline earth metal salts. Representative alkali or alkaline earth metal salts include sodium, lithium, potassium, calcium, magnesium, and the like. Further pharmaceutically acceptable salts include, when appropriate, nontoxic ammonium, quaternary ammonium, and amine cations formed using counterions such as halide, hydroxide, carboxylate, sulfate, phosphate, nitrate, loweralkyl sulfonate and aryl sulfonate. Other acids and bases, while not in themselves pharmaceutically acceptable, may be employed in the preparation of salts useful as intermediates in obtaining the compounds of the invention and their pharmaceutically acceptable acid or base addition salts.

Pharmaceutically acceptable carriers that may be used in these pharmaceutical compositions include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, sodium carboxymethylcellulose, polyacrylates, waxes, polyethylene-polyoxypropylene-block polymers, polyethylene glycol and wool fat.

The compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intraperitoneal, intrahepatic, intralesional and intracranial injection or infusion techniques.

Sterile injectable forms of the compositions of this invention may be aqueous or oleaginous suspension. These suspensions may be formulated according to techniques known in the art using suitable dispersing or wetting agents and suspending agents. The sterile injectable preparation may also be a sterile injectable solution or suspension in a nontoxic parenterally-acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium. For this purpose, a bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents which are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

The pharmaceutical compositions of this invention may be orally administered in any orally acceptable dosage form including, but not limited to, capsules, tablets, aqueous suspensions or solutions. In the case of tablets for oral use, carriers commonly used may include lactose and corn starch. Lubricating agents, such as magnesium stearate, may also be added. For oral administration in a capsule form, useful diluents may include lactose and dried cornstarch. When aqueous suspensions are required for oral use, the active ingredient may be combined with emulsifying and suspending agents. If desired, certain sweetening, flavoring or coloring agents may also be added.

Alternatively, the pharmaceutical compositions of this invention may be administered in the form of suppositories for rectal administration. These can be prepared by mixing the agent with a suitable non-irritating excipient which is solid at room temperature but liquid at rectal temperature and therefore will melt in the rectum to release the drug. Such materials may include cocoa butter, beeswax and polyethylene glycols.

The pharmaceutical compositions of this invention may also be administered topically, especially when the target of treatment includes areas or organs readily accessible by topical application, including diseases of the eye, the skin, or the lower intestinal tract. Suitable topical formulations may be prepared for each of these areas or organs.

Topical application for the lower intestinal tract can be effected in a rectal suppository formulation (see above) or in a suitable enema formulation. Topically-transdermal patches may also be used.

For topical applications, the pharmaceutical compositions may be formulated in a suitable ointment containing the active component suspended or dissolved in one or more carriers. Carriers for topical administration of the compounds of this invention may include, but are not limited to, mineral oil, liquid petrolatum, white petrolatum, propylene glycol, polyoxyethylene, polyoxypropylene compound, emulsifying wax and water. Alternatively, the pharmaceutical compositions may be formulated in a suitable lotion or cream containing the active components suspended or dissolved in one or more pharmaceutically acceptable carriers. Suitable carriers may include, but are not limited to, mineral oil, sorbitan monostearate, polysorbate 60, cetyl esters wax, cetearyl alcohol, 2-octyldodecanol, benzyl alcohol and water.

For ophthalmic use, the pharmaceutical compositions may be formulated as micronized suspensions in isotonic, pH adjusted sterile saline, or as solutions in isotonic, pH adjusted sterile saline, either with or without a preservative such as benzylalkonium chloride. Alternatively, for ophthalmic uses, the pharmaceutical compositions may be formulated in an ointment such as petrolatum.

The pharmaceutical compositions of this invention may also be administered by nasal aerosol or inhalation. Such compositions may be prepared as solutions in saline, employing benzyl alcohol or other suitable preservatives, absorption promoters to enhance bioavailability, fluorocarbons, and/or other conventional solubilizing or dispersing agents.

The amount of kinase inhibitor that may be combined with the carrier materials to produce a single dosage form will vary depending upon the host treated, the particular mode of administration, and the indication. In an embodiment, the compositions should be formulated so that a dosage of between 0.01-100 mg/kg body weight/day of the inhibitor can be administered to a patient receiving these compositions. In another embodiment, the compositions should be formulated so that a dosage of between 0.1-100 mg/kg body weight/day of the inhibitor can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated. The amount of inhibitor will also depend upon the particular compound in the composition.

According to another embodiment, the invention provides methods for treating or preventing cancer, a proliferative disorder, or a myeloproliferative disorder comprising the step of administering to a patient one of the herein-described compounds or pharmaceutical compositions.

The term "patient", as used herein, means an animal, including a human.

In some embodiments, said method is used to treat or prevent a hematopoietic disorder, such as acute-myelogenous leukemia (AML), acute-promyelocytic leukemia (APL), chronic-myelogenous leukemia (CML), or acute lymphocytic leukemia (ALL).

In other embodiments, said method is used to treat or prevent myeloproliferative disorders, such as polycythemia vera, thrombocythemia, myeloid metaplasia with myelofibrosis, chronic myelogenous leukaemia (CML), chronic myelomonocytic leukemia, hypereosinophilic syndrome, juvenile myelomonocytic leukemia, and systemic mast cell disease.

In yet other embodiments, said method is used to treat or prevent cancer, such as cancers of the breast, colon, prostate, skin, pancreas, brain, genitourinary tract, lymphatic system, stomach, larynx and lung, including lung adenocarcinoma, small cell lung cancer, and non-small cell lung cancer.

Another embodiment provides a method of treating or preventing cancer comprising the step of administering to a patient a compound of formula I or a composition comprising said compound.

Another aspect of the invention relates to inhibiting kinase activity in a patient, which method comprises administering to the patient a compound of formula I or a composition comprising said compound. In some embodiments, said kinase is an Aurora kinase (Aurora A, Aurora B, Aurora C), Abl, Arg, FGFR1, MELK, MLK1, MuSK, Ret, or TrkA.

Depending upon the particular conditions to be treated or prevented, additional drugs may be administered together with the compounds of this invention. In some cases, these additional drugs are normally administered to treat or prevent the same condition. For example, chemotherapeutic agents or other anti-proliferative agents may be combined with the compounds of this invention to treat proliferative diseases.

Another aspect of this invention is directed towards a method of treating cancer in a subject in need thereof, comprising the sequential or co-administration of a compound of this invention or a pharmaceutically acceptable salt thereof, and another therapeutic agent. In some embodiments, said additional therapeutic agent is selected from an anti-cancer agent, an anti-proliferative agent, or a chemotherapeutic agent.

In some embodiments, said additional therapeutic agent is selected from camptothecin, the MEK inhibitor: U0126, a KSP (kinesin spindle protein) inhibitor, adriamycin, interferons, and platinum derivatives, such as Cisplatin.

In other embodiments, said additional therapeutic agent is selected from taxanes; inhibitors of bcr-abl (such as Gleevec, dasatinib, and nilotinib); inhibitors of EGFR (such as Tarceva and Iressa); DNA damaging agents (such as cisplatin, oxaliplatin, carboplatin, topoisomerase inhibitors, and anthracyclines); and antimetabolites (such as AraC and 5-FU).

In one embodiment, said additional therapeutic agent is dasatnib or nilotinib.

In another embodiment, said additional therapeutic agent is dasatnib.

In another embodiment, said additional therapeutic agent is nilotinib.

In yet other embodiments, said additional therapeutic agent is selected from camptothecin, doxorubicin, idarubicin, Cisplatin, taxol, taxotere, vincristine, tarceva, the MEK inhibitor, U0126, a KSP inhibitor, vorinostat, Gleevec, dasatinib, and nilotinib.

In another embodiment, said additional therapeutic agent is selected from Her-2 inhibitors (such as Herceptin); HDAC inhibitors (such as vorinostat), VEGFR inhibitors (such as Avastin), c-KIT and FLT-3 inhibitors (such as sunitinib), BRAF inhibitors (such as Bayer's BAY 43-9006) MEK inhibitors (such as Pfizer's PD0325901); and spindle poisons (such as Epothilones and paclitaxel protein-bound particles (such as Abraxane®).

Other therapies or anticancer agents that may be used in combination with the inventive anticancer agents of the present invention include surgery, radiotherapy (in but a few examples, gamma-radiation, neutron beam radiotherapy, electron beam radiotherapy, proton therapy, brachytherapy, and systemic radioactive isotopes, to name a few), endocrine therapy, biologic response modifiers (interferons, interleukins, and tumor necrosis factor (TNF) to name a few), hyperthermia and cryotherapy, agents to attenuate any adverse effects (e.g., antiemetics), and other approved chemotherapeutic drugs, including, but not limited to, alkylating drugs (mechlorethamine, chlorambucil, Cyclophosphamide, Melphalan, Ifosfamide), antimetabolites (Methotrexate), purine antagonists and pyrimidine antagonists (6-Mercaptopurine, 5-Fluorouracil, Cytarabile, Gemcitabine), spindle poisons (Vinblastine, Vincristine, Vinorelbine, Paclitaxel), podophyllotoxins (Etoposide, Irinotecan, Topotecan), antibiotics (Doxorubicin, Bleomycin, Mitomycin), nitrosoureas (Carmustine, Lomustine), inorganic ions (Cisplatin, Carboplatin), enzymes (Asparaginase), and hormones (Tamoxifen, Leuprolide, Flutamide, and Megestrol), Gleevec™, dexamethasone, and cyclophosphamide.

A compound of the instant invention may also be useful for treating cancer in combination with the following therapeutic agents: abarelix (Plenaxis Depot®); aldesleukin (Prokine®); Aldesleukin (Proleukin®); Alemtuzumabb (Campath®); alitretinoin (Panretin®); allopurinol (Zyloprim®); altretamine (Hexylen®); amifostine (Ethyol®); anastrozole (Arimidex®); arsenic trioxide (Trisenox®); asparaginase (Elspar®); azacitidine (Vidaza®); bevacuzimab (Avastin®); bexarotene capsules (Targretin®); bexarotene gel (Targretin®); bleomycin (Blenoxane®); bortezomib (Velcade®); busulfan intravenous (Busulfex®); busulfan oral (Myleran®); calusterone (Methosarb®); capecitabine (Xeloda®); carboplatin (Paraplatin®); carmustine (BCNU®, BiCNU®); carmustine (Gliadel®); carmustine with Polifeprosan 20 Implant (Gliadel Wafer®); celecoxib (Celebrex®); cetuximab (Erbitux®); chlorambucil (Leukeran®); cisplatin (Platinol®); cladribine (Leustatin®, 2-CdA®); clofarabine (Clolar®); cyclophosphamide (Cytoxan®, Neosar®); cyclophosphamide (Cytoxan Injection®); cyclophosphamide (Cytoxan Tablet®); cytarabine (Cytosar-U®); cytarabine liposomal (DepoCyt®); dacarbazine (DTIC-Dome®); dactinomycin, actinomycin D (Cosmegen®); Darbepoetin alfa (Aranesp®); daunorubicin liposomal (DanuoXome®); daunorubicin, daunomycin (Daunorubicin®); daunorubicin, daunomycin (Cerubidine®); Denileukin diftitox (Ontak®); dexrazoxane (Zinecard®); docetaxel (Taxotere®); doxorubicin (Adriamycin PFS®); doxorubicin (Adriamycin®, Rubex®); doxorubicin (Adriamycin PFS Injection®); doxorubicin liposomal (Doxil®); dromostanolone propionate (Dromostanolone®); dromostanolone propionate (Masterone Injection®); Elliott's B Solution (Elliott's B Solution®); epirubicin (Ellence®); Epoetin alfa (Epogen®); erlotinib (Tarceva®); estramustine (Emcyt®); etoposide phosphate (Etopophos®); etoposide, VP-16 (Vepesid®); exemestane (Aromasin®); Filgrastim (Neupogen®); floxuridine (intraarterial) (FUDR®); fludarabine (Fludara®); fluorouracil, 5-FU (Adrucil®); fulvestrant (Faslodex®); gefitinib (Iressa®); gemcitabine (Gemzar®); gemtuzumab ozogamicin (Mylotarg®); goserelin acetate (Zoladex Implant®); goserelin acetate (Zoladex®); histrelin acetate (Histrelin Implant®); hydroxyurea (Hydrea®); Ibritumomab Tiuxetan (Zevalin®); idarubicin (Idamycin®); ifosfamide (IFEX®); imatinib mesylate (Gleevec®); interferon alfa 2a (Roferon A®); Interferon alfa-2b (Intron A®); irinotecan (Camptosar®); lenalidomide (Revlimid®); letrozole (Femara®); leucovorin (Wellcovorin®) Leucovorin®); Leuprolide Acetate (Eligard®); levamisole (Ergamisol®); lomustine, CCNU (CeeBU®); meclorethamine, nitrogen mustard (Mustargen®); megestrol acetate (Megace®); melphalan, L-PAM (Alkeran®); mercaptopurine, 6-MP (Purinethol®); mesna (Mesnex®); mesna (Mesnex Tabs®); methotrexate (Methotrexate®); methoxsalen (Uvadex®); mitomycin C (Mutamycin®); mitotane (Lysodren®); mitoxantrone (Novantrone®); nandrolone phenpropionate (Durabolin-50®); nelarabine (Arranon®); Nofetumomab (Verluma®); Oprelvekin (Neumega®); oxaliplatin (Eloxatin®); paclitaxel (Paxene®); paclitaxel (Taxol®); paclitaxel protein-bound particles (Abraxane®); palifermin (Kepivance®); pamidronate (Aredia®); pegademase (Adagen (Pegademase Bovine)®); pegaspargase (Oncaspar®); Pegfilgrastim (Neulasta®); pemetrexed disodium (Alimta®); pentostatin (Nipent®); pipobroman (Vercyte®); plicamycin, mithramycin (Mithracin®); porfimer sodium (Photofrin®); procarbazine (Matulane®); quinacrine (Atabrine®); Rasburicase (Elitek®); Rituximab (Rituxan®); sargramostim (Leukine®); Sargramostim (Prokine®); sorafenib (Nexavar®); streptozocin (Zanosar®); sunitinib maleate (Sutent®); talc (Sclerosol®); tamoxifen (Nolvadex®); temozolomide (Temodar®); teniposide, VM-26 (Vumon®); testolactone (Teslac®); thioguanine, 6-TG (Thioguanine®); thiotepa (Thioplex®); topotecan (Hycamtin®); toremifene (Fareston®); Tositumomab (Bexxar®); Tositumomab/I-131 tositumomab (Bexxar®); Trastuzumab (Herceptin®); tretinoin, ATRA (Vesanoid®); Uracil Mustard (Uracil Mustard Capsules®); valrubicin (Valstar®); vinblastine (Velban®); vincristine (Oncovin®); vinorelbine (Navelbine®); zoledronate (Zometa®) and vorinostat (Zolinza®).

For a comprehensive discussion of updated cancer therapies see, http://www.nci.nih.gov/, a list of the FDA approved oncology drugs at http://www.fda.gov/cder/cancer/druglistframe.htm, and The Merck Manual, Seventeenth Ed. 1999, the entire contents of which are hereby incorporated by reference.

Another embodiment provides a simultaneous, separate or sequential use of a combined preparation.

Those additional agents may be administered separately, as part of a multiple dosage regimen, from the kinase inhibitor-containing compound or composition. Alternatively, those agents may be part of a single dosage form, mixed together with the kinase inhibitor in a single composition.

In order that this invention be more fully understood, the following preparative and testing examples are set forth. These examples are for the purpose of illustration only and are not to be construed as limiting the scope of the invention in any way. All documents cited herein are hereby incorporated by reference.

EXAMPLES

As used herein, the term "Rt(min)" refers to the HPLC retention time, in minutes, associated with the compound. Unless otherwise indicated, the HPLC method utilized to obtain the reported retention time is as follows:
  Column: ACE C8 column, 4.6×150 mm
  Gradient: 0-100% acetonitrile+methanol 60:40 (20 mM Tris phosphate)
  Flow rate: 1.5 mL/minute
  Detection: 225 nm.

Mass spec. samples were analyzed on a MicroMass Quattro Micro mass spectrometer operated in single MS mode with electrospray ionization. Samples were introduced into the mass spectrometer using chromatography. Mobile phase for all mass spec. analyses consisted of 10 mM pH 7 ammonium acetate and a 1:1 acetonitrile-methanol mixture, column gradient conditions was 5%-100% acetonitrile-methanol over 3.5 mins gradient time and 5 mins run time on an ACE C8 3.0×75 mm column. Flow rate was 1.2 ml/min.

$^1$H-NMR spectra were recorded at 400 MHz using a Bruker DPX 400 instrument. The following compounds of formula I were prepared and analyzed as follows.

Example 1

Scheme 2.

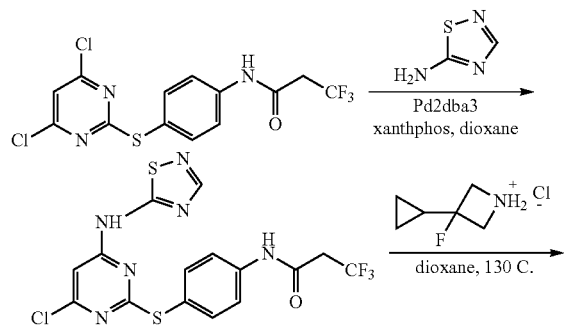

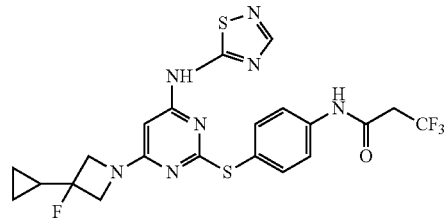

N-(4-(4-(1,2,4-thiadiazol-5-ylamino)-6-(3-cyclopropyl-3-fluoroazetidin-1-yl)pyrimidin-2-ylthio)phenyl)-3,3,3-trifluoropropanamide (Compound I-1)

I-1

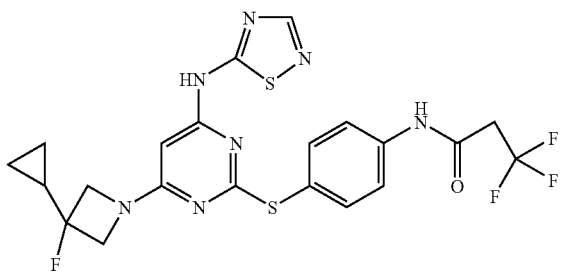

N-(4-(4-(1,2,4-thiadiazol-5-ylamino)-6-chloropyrimidin-2-ylthio)phenyl)-3,3,3-trifluoropropanamide

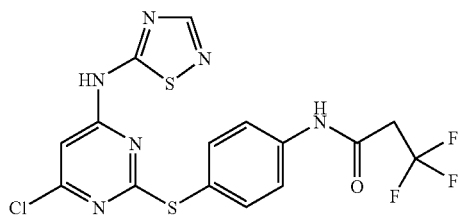 [SMILES: O=C(CC(F)(F)F)Nc1ccc(Sc2nc(Cl)cc(Nc3ncns3)n2)cc1]

To a round bottom flask was added N-(4-(4,6-dichloropyrimidin-2-ylthio)phenyl)-3,3,3-trifluoropropanamide (350 mg, 0.9 mmol), 1,2,4-thiadiazole-5-amine (100 mg, 0.9 mmol), xanthphos (50 mg, 0.1 mmol), Pd$_2$dba$_3$ (50 mg, 0.05 mmol), NaCO$_3$ (150 mg, 1.5 mmol) and dioxane(10 cm). The mixture was flushed with nitrogen and then brought to reflux for 2 hours. The mixture was filtered, partitioned between ethylacetate and bicarbonate. The organic layer was dried with magnesium sulfate, and concentrated to an oil, which was purified by column chromatography to yield the product as a yellow solid (127 mg, 34%)

23

N-(4-(4-(1,2,4-thiadiazol-5-ylamino)-6-(3-cyclopropyl-3-fluoroazetidin-1yl)pyrimidin-2-ylthio)phenyl)-3,3,3-trifluoropropanamide

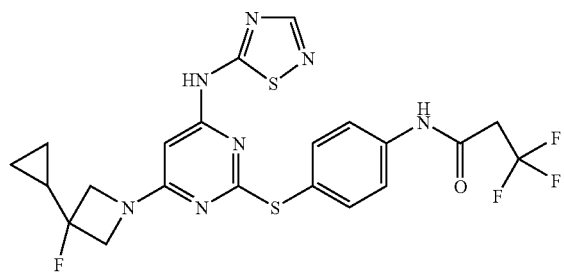 [SMILES: O=C(CC(F)(F)F)Nc1ccc(Sc2nc(Nc3ncns3)cc(N3CC(F)(C4CC4)C3)n2)cc1]

24

To a microwave tube was added N-(4-(4-(1,2,4-thiadiazol-5-ylamino)-6-chloropyrimidin-2-ylthio)phenyl)-3,3,3-trifluoropropanamide (100 mg, 0.25 mmol), 3-cyclopropyl-3-fluoroazetidine hydrochloride (100 mg, 0.7 mmol), DIPEA (0.1 ml) and dioxane. The mixture was microwaved at 130 C for 20 mins, partitioned between ethylacetate and bicarbonate and organic layer concentrated to an oil. The product was purified by HPLC to afford the product as a white solid (27 mg, 20%) $^1$H NMR d$_6$ DMSO 0.42-0.48 (2H, m), 0.6-0.63 (2H, m), 1.38-1.43 (1H, m), 3.55-3.65 (2H, m), 3.8-4.0 (4H, m), 5.65 (1H,s), 7.65 (2H, d), 7.75 (2H, d), 8.2 (1H,s), 10.7 (1H,s), 12.1 (1H,s); MS ESI+ve 526 (M+H)$^+$.

Example 2

Scheme 3.

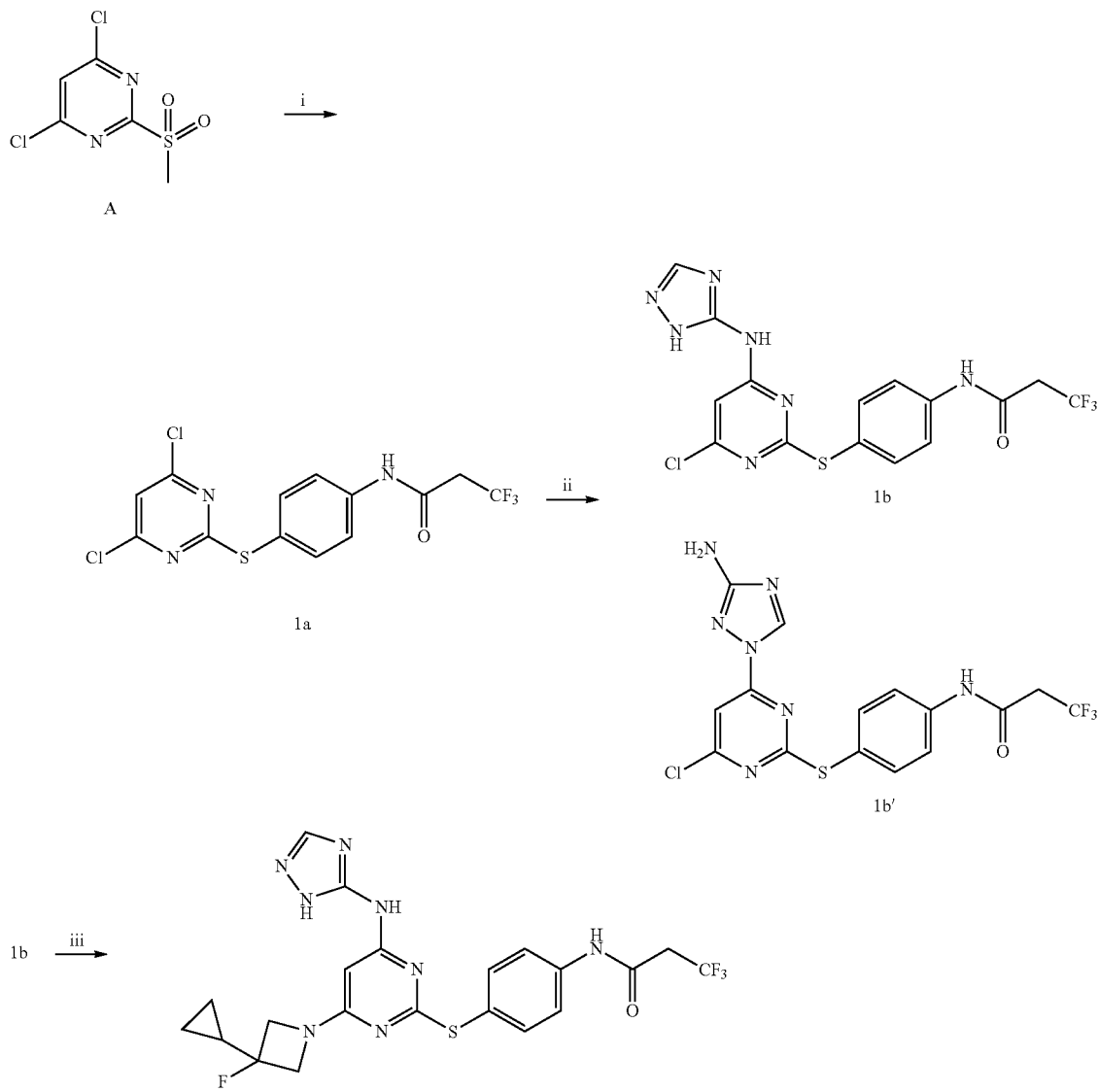

i. Sulfide, TEA, acetonitrile;
ii. Amine, Pd$_2$dba$_3$, Xantphos, sodium carbonate, 1,4-dioxane, microwave, 120° C., 1 hour;
iii. Amine, DiPEA, 1,4-dioxane, microwave, 140° C., 30 minutes.

N-(4-(4-(4H-1,2,4-Triazol-3-ylamino)-6-(3-cyclopropyl-3-fluoroazetidin-1-yl)pyrimidin-2-ylthio)phenyl)-3,3,3-trifluoropropanamide (Compound I-2)

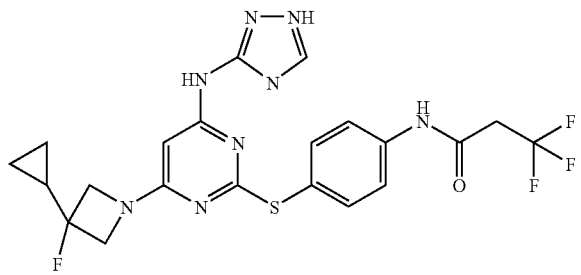

N-(4-(4,6-Dichloropyrimidin-2-ylthio)phenyl)-3,3,3-trifluoropropanamide (1a)

To a cold solution (−10° C.) of 4,6-dichloromethylsulfonylpyrimidine (8 grams, 35.2 mmol) and 3,3,3-trifluoro-N-(4-mercaptophenyl)propanamide (8.7 grams, 37 mmol, 1.05 eq.) in acetonitrile (250 mL) was added Et$_3$N (4.9 mL) dropwise over 20 minutes. The mixture was stirred at −10° C. for 20 minutes after addition of the Et$_3$N and allowed to warm to RT. After concentration to approximately 150 mL, H$_2$O (250 mL) was added and the resulting suspension was filtered. The residue was dried by suction and in vacuo, slurried in a minimum of EtOAc, filtered and dried by suction and in vacuo. Yield was 7.3 grams (50%) of an off-white solid.

$^1$H-NMR (300 MHz, DMSO-d$_6$): δ 10.53 (bs, 1H); 7.68 (d, J=9.35 Hz, 2H); 7.56 (d, J=8.8 Hz, 2H); 3.54 (q, J=11 Hz, 2H) ppm.

N-(4-(4-(2H-1,2,4-Triazol-3-ylamino)-6-chloropyrimidin-2-ylthio)phenyl)-3,3,3-trifluoropropanamide (1b) and N-(4-(4-(3-amino-1H-1,2,4-triazol-1-yl)-6-chloropyrimidin-2-ylthio)phenyl)-3,3,3-trifluoropropanamide (1b')

Nitrogen was bubbled through a mixture of 1a (2.0 g, 5.2 mmol), 3-amino-1H-1,2,4-triazole (0.48 g, 5.8 mmol), tris(dibenzylideneacetone)dipalladium(0) (Pd$_2$ dba$_3$, 0.24 g, 0.26 mmol), 9,9-dimethyl-4,5-bis(diphenylphosphino)xanthene (xantphos, 0.3 g, 0.52 mmol), sodium carbonate (0.77 g, 7.3 mmol) in 1,4-dioxane (35 mL). The mixture was heated in the microwave to 130° C. for 2 hours. HPLC indicated complete conversion and the formation of two peaks with the correct mass (at 7.84 min and at 8.54 min). The mixture was filtered through Celite and rinsed with 1,4-dioxane. The solvent was removed under reduced pressure and the residue was coated on silica (by dissolving it in dichloromethane/methanol). The coated material was brought on a column and eluted with a gradient of 2-propanol (5-7%) in dichloromethane. Three fractions were obtained. The second (1b', 280 mg, purity 86% purity, HPLC method A: Rf=8.548 minutes) and the third (700 mg) were product fractions. The third fraction needed an additional column purification (SiO$_2$, dichloromethane/4-7% 2-propanol) to yield 450 mg of 1b with 49-68% purity (HPLC method A: Rf=7.843 minutes).

N-(4-(4-(4H-1,2,4-Triazol-3-ylamino)-6-(3-cyclopropyl-3-fluoroazetidin-1-yl)pyrimidin-2-ylthio)phenyl)-3,3,3-trifluoropropanamide (Compound I-2)

A mixture of compound 1b (240 mg, 0.56 mmol), 3-cyclopropyl-3-fluoroazetidine hydrochloric acid (127 mg, 0.84 mmol), and N,N-diisopropylethylamine (0.24 mL, 1.4 mmol) in 1,4-dioxane (5 mL) was heated in the microwave to 130° C. for 30 minutes. The mixture was evaporated to dryness under reduced pressure and then coated on silica by dissolving it first in a mixture of dichloromethane and methanol. The coated material was brought on a column that was eluted with a gradient of 2-propanol (3-6%) in dichloromethane to yield 55 mg of N-(4-(4-(4H-1,2,4-triazol-3-ylamino)-6-(3-cyclopropyl-3-fluoroazetidin-1-yl)pyrimidin-2-ylthio)phenyl)-3,3,3-trifluoropropanamide with a purity of 93/95% (HPLC method A, Rf=8.513 minutes).

$^1$H-NMR (300 MHz, DMSO-d$_6$): 10.52 (s, 1H); 7.71-7.57 (m, 5H); 3.99-3.82 (m, 4H); 3.58 (q, J=10.7 Hz, 2H); 1.50-1.35 (m, 1H); 0.62-0.56 (m, 2H); 0.44-1.40 (m, 2H) ppm.

Example 3

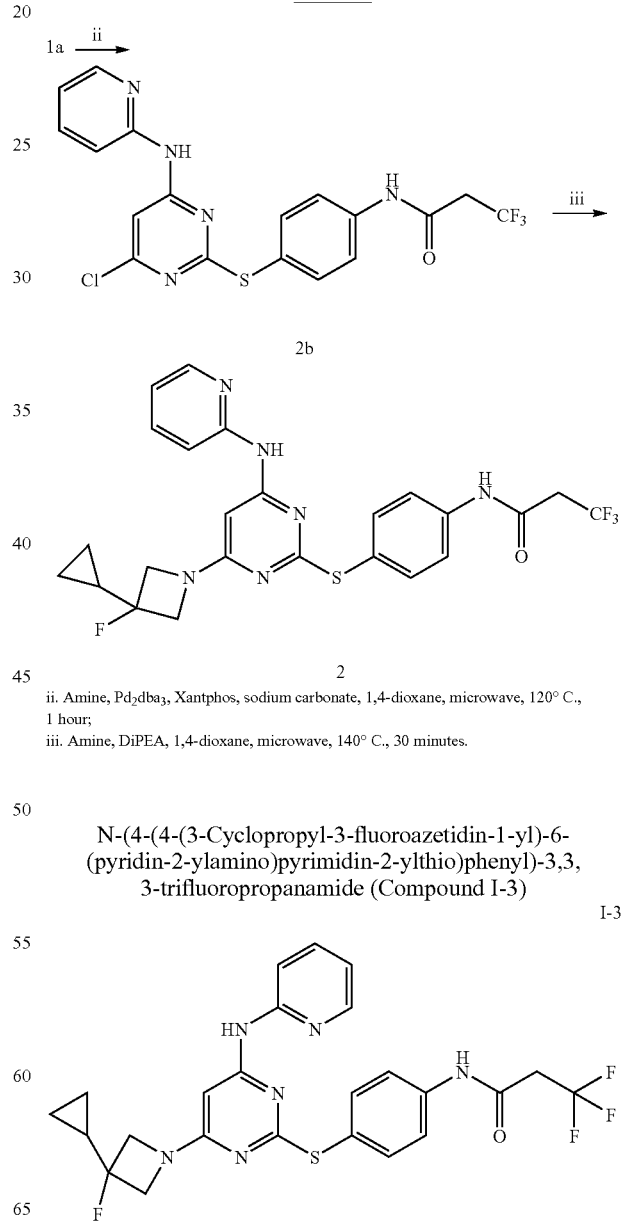

ii. Amine, Pd$_2$dba$_3$, Xantphos, sodium carbonate, 1,4-dioxane, microwave, 120° C., 1 hour;
iii. Amine, DiPEA, 1,4-dioxane, microwave, 140° C., 30 minutes.

N-(4-(4-(3-Cyclopropyl-3-fluoroazetidin-1-yl)-6-(pyridin-2-ylamino)pyrimidin-2-ylthio)phenyl)-3,3,3-trifluoropropanamide (Compound I-3)

As described in Scheme 4, N-(4-(4-Chloro-6-(pyridin-2-ylamino)pyrimidin-2-ylthio)phenyl)-3,3,3-trifluoropropanamide N-(4-(4,6-dichloropyrimidin-2-ylthio)phenyl)-3,3,3-trifluoropropanamide (1a, 400 mg, 1.04 mmol), aminopyridine (99 mg, 1.04 mmol, 1 eq.), xantphos (68 mg, 0.12 mmol, 11 mol %), Pd$_2$(dba)$_3$ (53 mg, 0.057 mmol, 5.5 mol %) and Na$_2$CO$_3$ (189 mg, 1.78 mmol, 1.7 eq.) were transferred to a microwave vial and 1,4-dioxane (15 mL) was added. The mixture was flushed with N$_2$ for 20 minutes while stirring. The vial was capped and heated at 120° C. for 1 hour, HPLC-MS analysis showed 41-66% product in the mixture. The mixture was filtered and concentrated, yielding 620 mg (>100%) of a yellow oil which partly crystallized upon standing. The product was used without further purification, purity: 41-61% (HPLC method A, Rf=8.471 minutes).

N-(4-(4-chloro-6-(pyridin-2-ylamino)pyrimidin-2-ylthio)phenyl)-3,3,3-trifluoropropanamide (2b, 620 mg, 1.4 mmol) and 3-cyclopropyl-3-fluoroazetidine hydrochloride (598 mg, 3.94 mmol, 2.8 eq.) were dissolved in 1,4-dioxane and transferred to a microwave vial. DiPEA (437 mg, 3.38 mmol, 2.4 eq.) was added. The mixture was flushed with N$_2$ for 10 minutes while stirring and heated at 140° C. for 30 minutes in the microwave. HPLC-MS analysis showed 27-40% product in the mixture. The mixture was concentrated and purified by preparative HPLC and lyophilized, yielding 28 mg (3.8%) of a light-yellow solid with a purity of 98+% (HPLC method B: Rf=5.855 minutes).

$^1$H-NMR (300 MHz, DMSO-d$_6$): δ 10.6 (s, 1H); 9.6 (s, 1H); 8.14 (d, J=4.7 Hz, 1H); 7.68 (d, J=8.6 Hz, 2H); 7.56 (d, J=8.6 Hz, 2H); 7.24-7.18 (m, 2H); 6.81-6.77 (m, 1H); 6.02 (s, 1H); 4.0-3.83 (m, 4H); 3.57 (q, J=11.2 Hz, 2H); 1.42 (m, 1H); 0.64-0.58 (m, 2H); 0.47-0.42 (m, 2H) ppm.

Example 4

Scheme 5.

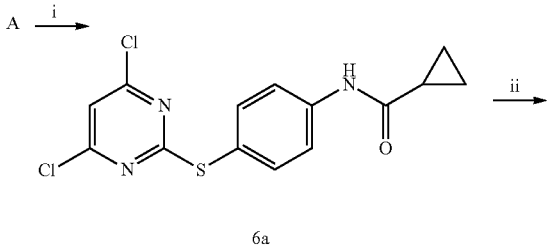

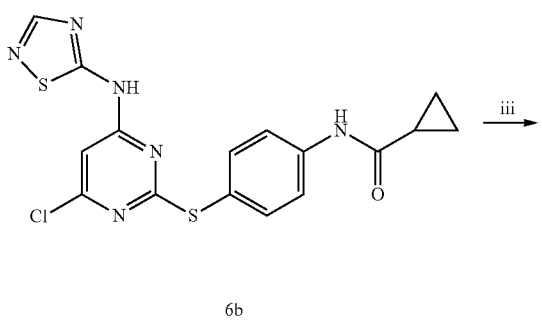

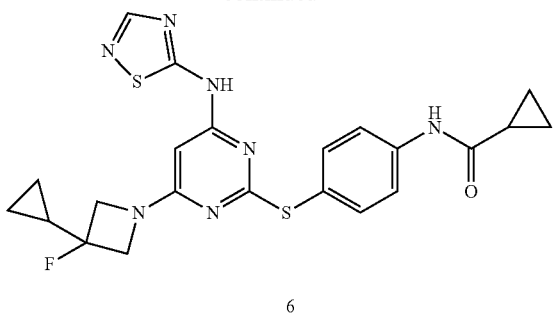

i. Sulfide, TEA, acetonitrile;
ii. Amine, Pd$_2$dba$_3$, Xantphos, sodium carbonate,1,4-dioxane, microwave, 120° C., 1 hour;
iii. Amine, DiPEA, 1,4-dioxane, microwave, 140° C., 30 minutes.

N-(4-(4-(1,2,4-Thiadiazol-5-ylamino)-6-(3-cyclopropyl-3-fluoroazetidin-1-yl)pyrimidin-2-ylthio)phenyl)cyclopropanecarboxamide (Compound I-4)

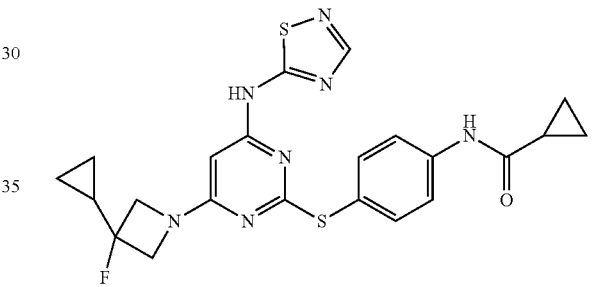

A mixture of N-(4-(4,6-dichloropyrimidin-2-ylthio)phenyl)-cycloproponamide (350 mg, 0.9 mmol), 1,2,4,-thiadiazole-5-amine (100 mg, 0.9 mmol), Pd$_2$ dba$_3$ (50 mg), xantphos (50 mg), sodium carbonate (150 mg, 1.5 mmol) in 1,4-dioxane was flushed with nitrogen for 15 minutes and then heated in the microwave to 140° C. for 1 hour. The reaction mixture was filtered and evaporated to dryness. The residue (780 mg) was used as such in the next step, purity 33-37% (HPLC method A, Rf=8.016 minutes).

A mixture of crude N-(4-(4-(1,2,4-Thiadiazol-5-ylamino)-6-chloropyrimidin-2-ylthio)phenyl)cyclopropanecarboxamide (780 mg, 1.93 mmol), 3-cyclopropyl -3-fluoroazetidine hydrochloride (818 mg, 5.4 mmol), DiPEA (0.7 mL, 4.6 mmol) in 1,4-dioxane (20 mL) was heated in the microwave to 130° C. for 20 minutes. The mixture was concentrated and purified by preparative HPLC to yield 34 mg of N-(4-(4-(1,2,4-Thiadiazol-5-ylamino)-6-(3-cyclopropyl-3-fluoroazetidin-1-yl)pyrimidin-2-ylthio)phenyl)cyclopropanecarboxamide with a purity of 95+% (HPLC method A, Rf=8.573 minutes).

$^1$H-NMR (300 MHz, DMSO-d$_6$): δ 10.4 (bs, 1H); 8.11 (s, 1H); 7.71 (d, J=8.7 Hz, 2H); 7.52 (d, J=8.7 Hz, 2H); 5.61 (bs, 1H); 4.04-3.94 (m, 4H); 1.96 (bd, 1H); 1.84-1.80 (m, 1H); 1.50-1.37 (m, 1H); 0.84-0.82 (m, 4H); 0.62-0.59 (m, 2H); 0.47-0.44 (m, 2H) ppm.

Example 5

N-(4-(4-(3-Cyclopropyl-3-fluoroazetidin-1-yl)-6-(pyridin-2-ylamino)pyrimidin-2-ylthio)phenyl)cyclopropanecarboxamide (Compound I-5)

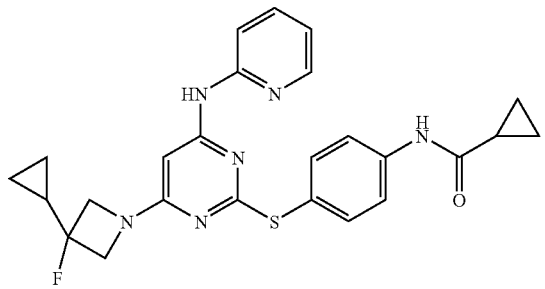

I-5

A mixture of N-(4-(4,6-dichloropyrimidin-2-ylthio)phenyl)-cyclopropanamide (200 mg, 0.6 mmol), 2-aminopyridine (61 mg, 0.65 mmol), Pd2 dba3 (28 mg), xantphos (35 mg), and sodium carbonate (89 mg, 0.84 mmol) in 1,4-dioxane (5 mL). The crude product was purified by ISCO (gradient methanol in dichloromethane) to yield 110 mg of N-(4-(4-Chloro-6-(pyridin-2-ylamino)pyrimidin-2-ylthio)phenyl)cyclopropanecarboxamide with ~30% purity (HPLC method A, Rf=8.493 minutes) that was used without further purification in the next step.

Prepared according the procedure used for the synthesis of compound I-1, starting with N-(4-(4-Chloro-6-(pyridin-2-ylamino)pyrimidin-2-ylthio)phenyl)cyclopropane carboxamide (110 mg, 28 mmol), 3-cyclopropyl-3-fluoroazetidine hydrochloride (60 mg, 0.39 mmol), and DiPEA (0.15 mL, 0.9 mmol) in 1,4-dioxane. After column chromatography, the product containing fraction (TLC: SiO2, dichloromethane/7.5% 2-propanol, Rf=0.65; HPLC: 70/90% purity, Rf=8.813 minutes) was purified further by preparative HPLC to yield 4 mg after evaporation and lyophilization with a purity of 96+% (HPLC method B, Rf=5.841 minutes).

$^1$H-NMR (300 MHz, CD$_3$OD): δ 7.99 (d, J=4.4 Hz, 1H); 7.58 (d, J=8.7 Hz, 2H); 7.44 (d, J=8.7 Hz, 2H); 7.23-7.13 (m, 2H); 6.72-6.66 (m, 1H); 5.73 (s, 1H); 4.74-3.24 (m, 4H); 1.75-1.71 (m, 1H); 1.31-1.11 (m, 2H); 0.93-0.77 (m, 4H); 0.59-0.41 (m, 2H); 0.41-0.36 (m, 2H) ppm.

Example 6

N-(4-(4-(4H-1,2,4-Triazol-3-ylamino)-6-(3-cyclopropyl-3-fluoroazetidin-1-yl)pyrimidin-2-ylthio)phenyl)cyclopropanecarboxamide (Compound I-6)

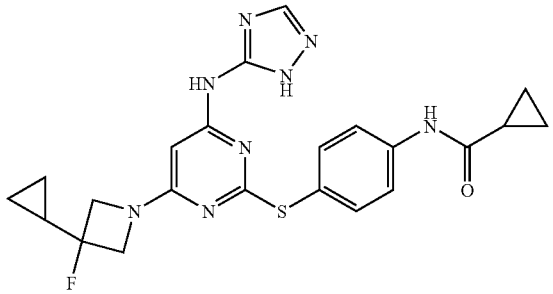

I-6

N-(4-(4-(2H-1,2,4-Triazol-3-ylamino)-6-chloropyrimidin-2-ylthio)phenyl)cyclopropanecarboxamide and N-(4-(4-(3-amino-1H-1,2,4-triazol-1-yl)-6-chloropyrimidin-2-ylthio)phenyl)cyclopropanecarboxamide were prepared according to the procedure used for compounds 1b and 1b' in Scheme 2 with N-(4-(4,6-dichloropyrimidin-2-ylthio)phenyl)-cyclopropanamide (1.0 g, 2.3 mmol), 3-amino-1H-1,2,4-triazole (270 mg, 3.2 mmol), Pd$_2$ dba$_3$ (140 mg), xantphos (173 mg), sodium carbonate (500 mg, 4.7 mmol) in 1,4-dioxane (15 mL). Two products were formed (HPLC method A: Rf=7.602 minutes and 8.444 minutes). These were separated by column chromatography (SiO$_2$, dichloromethane/3-10% 2-propanol; TLC: SiO$_2$, dichloromethane/7.5% 2-propanol, Rf=0.4 and Rf=0.3) to yield 170 mg of N-(4-(4-(3-amino-1H-1,2,4-triazol-1-yl)-6-chloropyrimidin-2-ylthio)phenyl)cyclopropanecarboxamide (HPLC method A: Rf=8.494 minutes) and 140 mg of N-(4-(4-(2H-1,2,4-Triazol-3-ylamino)-6-chloropyrimidin-2-ylthio)phenyl)cyclopropanecarboxamide (HPLC method A: Rf=7.700 minutes). N-(4-(4-(3-amino-1H-1,2,4-triazol-1-yl)-6-chloropyrimidin-2-ylthio)phenyl)cyclopropanecarboxamide: $^1$H-NMR (300 MHz, DMSO-d$_6$): δ 10.41 (s, 1H); 7.81-7.54 (m, 5H); 6.61 (s, 1H); 1.82-1.80 (m, 1H); 0.84-0.82 (m, 4H) ppm. N-(4-(4-(2H-1,2,4-Triazol-3-ylamino)-6-chloropyrimidin-2-ylthio)phenyl)cyclopropanecarboxamide: $^1$H-NMR (300 MHz, DMSO-d$_6$): δ 10.44 (s, 1H); 7.79-7.57 (m, 4H); 7.40 (s, 1H); 6.99 (s, 1H); 1.86-1.80 (m, 1H); 0.85-0.83 (m, 4H) ppm.

Compound I-6 was prepared according to the procedure of compound I-1 using N-(4-(4-(2H-1,2,4-Triazol-3-ylamino)-6-chloropyrimidin-2-ylthio)phenyl)cyclopropanecarboxamide (140 mg, 0.36 mmol), 3-cyclopropyl-3-fluoroazetidine hydrochloride (62 mg), DiPEA (0.14 mL) in 1,4-dioxane (5 mL). After purification by column chromatography, the obtained material was further purified by preparative HPLC to yield 18 mg of desired product after evaporation and lyophilization, purity: 99+% (HPLC method A, Rf=8.466 minutes).

$^1$H-NMR (300 MHz, DMSO-d$_6$): δ 10.43 (s, 1H); 7.84 (s, 1H); 7.72 (d, J=8.5 Hz, 2H); 7.54 (d, J=8.5 Hz, 2H); 6.02 (s, 1H); 3.99-3.82 (m, 4H); 1.85-1.81 (m, 1H); 1.43-1.39 (m, 1H); 0.84-0.82 (m, 4H); 0.61-0.58 (m, 2H); 0.44-0.42 (m, 2H) ppm

Example 7

N-(4-(4-(1,2,4-Thiadiazol-5-ylamino)-6-(azetidin-1-yl)pyrimidin-2-ylthio)phenyl)-2-chlorobenzamide (Compound I-7)

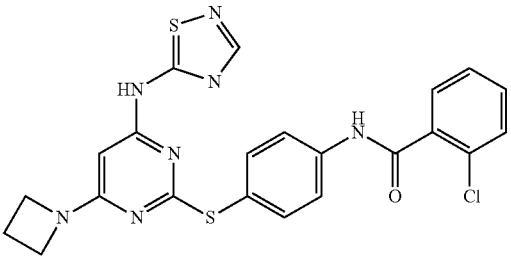

I-7

2-Chloro-N-(4-(4,6-dichloropyrimidin-2-ylthio)phenyl)benzamide (300 mg, 0.73 mmol), 1,2,4-thiadiazole-5-amine (74 mg, 0.73 mmol), Pd2 dba3 (36 mg), xantphos (46 mg), sodium carbonate (128 mg, 1.21 mmol) in 1,4-dioxane (10 mL) were flushed for 15 minutes with nitrogen and then heated in the microwave to 130° C. for 2 hours. The crude reaction mixture was poured in methanol, filtered through Celite and concentrated. Ethyl acetate and saturated aqueous sodium bicarbonate were added and the organic layer was dried over sodium sulfate, filtered, and concentrated to dryness to yield 380 mg N-(4-(4-(1,2,4-thiadiazol-5-ylamino)-6-chloropyrimidin-2-ylthio)phenyl)-2-chlorobenzamide with 50-60% purity (HPLC method A, Rf=8.576 minutes) that was used as such in the next step.

In the next step, a mixture of N-(4-(4-(1,2,4-thiadiazol-5-ylamino)-6-chloropyrimidin-2-ylthio)phenyl)-2-chlorobenzamide (188 mg, 0.42 mmol), azetidine (67.5 mg, 1.18 mmol), DiPEA (0.17 mL, 1.0 mmol) in 1,4-dioxane (10 mL) was heated to 130° C. for 20 minutes. The crude product (940 mg) was purified by preparative HPLC to yield 27 mg of N-(4-(4-(1,2,4-Thiadiazol-5-ylamino)-6-(azetidin-1-yl)pyrimidin-2-ylthio)phenyl)-2-chlorobenzamide with 99+% purity (HPLC method B, Rf=7.183 minutes).

$^1$H-NMR (300 MHz, DMSO-d$_6$): δ 10.63 (bs, 1H); 8.05 (s, 1H); 7.78 (d, 2H); 7.55-7.39 (m, 6H); 5.45 (s, 1H); 3.9 (m, 4H); 2.25 (m, 2H) ppm.

Example 8

4-(4-(1,2,4-Thiadiazol-5-ylamino)-6-(3-cyclopropyl-3-fluoroazetidin-1-yl)pyrimidin-2-ylthio)-N-(2,2,2-trifluoroethyl)benzamide (Compound I-8)

I-8

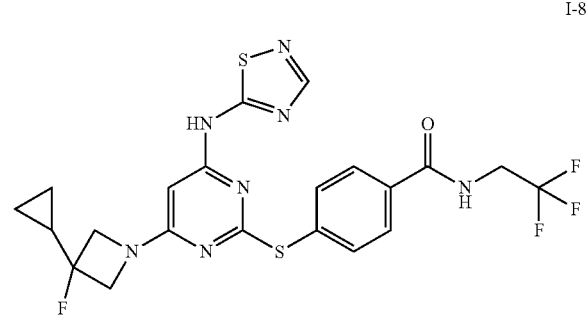 [SMILES: O=C(NCC(F)(F)F)c1ccc(Sc2nc(Nc3ncns3)cc(N3CC(F)(C4CC4)C3)n2)cc1]

4-(4,6-Dichloropyrimidin-2-ylthio)-N-(2,2,2-trifluoroethyl)benzamide was prepared according the procedure of 1a in Scheme 2 from 4,6-dichloromethylsulfonylpyrimidine (1.0 g, 4.4 mmol), 4-mercapto-N-(2,2,2-trifluoroethyl)benzamide (1.1 g, 4.7 mmol), and triethylamine (0.7 mL, 4.9 mmol) in acetonitrile (30 mL). Desired compound was purified by column chromatography (SiO2, ethyl acetate/heptanes=1:1-1:0, TLC: SiO2) to yield 210 mg (12%) (HPLC method A: Rf=8.508 minutes).

4-(4-(1,2,4-Thiadiazol-5-ylamino)-6-chloropyrimidin-2-ylthio)-N-(2,2,2-trifluoroethyl)benzamide was prepared according to the procedure for 1b in Scheme 2 using 4-(4,6-dichloropyrimidin-2-ylthio)-N-(2,2,2-trifluoroethyl)benzamide (210 mg, 0.55 mmol), 5-amino-1,2,4-thiadiazole (61 mg, 0.6 mmol), sodium carbonate (82 mg, 0.77 mmol), Pd2 dba3 (25 mg), xantphos (32 mg) in 1,4-dioxane (10 mL). After purification by column chromatography (SiO2, dichloromethane/5-7% 2-propanol) 120 mg of desired product was obtained, purity: 35-51% (HPLC method A: Rf=8.016 minutes). 4-(4-(1,2,4-Thiadiazol-5-ylamino)-6-(3-cyclopropyl-3-fluoroazetidin-1-yl)pyrimidin-2-ylthio)-N-(2,2,2-trifluoroethyl)benzamide was prepared according to the procedure for compound I-1 using 4-(4-(1,2,4-thiadiazol-5-ylamino)-6-chloropyrimidin-2-ylthio)-N-(2,2,2-trifluoroethyl)benzamide (120 mg, 0.27 mmol), 3-cyclopropyl-3-fluoroazetidine hydrochloride (60 mg, 0.4 mmol), DiPEA (0.05 mL, 0.67 mmol), in 1,4-dioxane (2 mL). After column chromatography (SiO2, dichloromethane/3-6% 2-propanol) about 60 mg were obtained with ~70% purity. This was further purified by preparative HPLC to yield 10 mg after evaporation and lyophilization with 88-87% purity (HPLC method A, Rf=8.694 minutes).

$^1$H-NMR (300 MHz, DMSO-d$_6$): δ 9.21 (t, J=5.6 Hz, 1H); 8.16 (s, 1H); 7.99 (d, J=8.4 Hz, 2H); 7.77 (d, J=8.4 Hz, 2H); 5.68 (s, 1H); 4.18-3.89 (m, 6H); 1.46-1.40 (m, 1H); 0.65-0.60 (m, 2H); 0.46-0.42 (m, 2H) ppm.

Example 9

Aurora-2 (Aurora A) Inhibition Assay

Compounds were screened for their ability to inhibit Aurora-2 using a standard coupled enzyme assay (Fox et al., Protein Sci., (1998) 7, 2249). Assays were carried out in a mixture of 100 mM Hepes (pH7.5), 10 mM MgCl$_2$, 1 mM DTT, 25 mM NaCl, 2.5 mM phosphoenolpyruvate, 300 µM NADH, 30 µg/ml pyruvate kinase and 10 µg/ml lactate dehydrogenase. Final substrate concentrations in the assay were 400 µM ATP (Sigma Chemicals) and 570 µM peptide (Kemptide, American Peptide, Sunnyvale, Calif.). Assays were carried out at 30° C. and in the presence of 40 nM Aurora-2.

An assay stock buffer solution was prepared containing all of the reagents listed above, with the exception of Aurora-2 and the test compound of interest. 55 µl of the stock solution was placed in a 96 well plate followed by addition of 2 µl of DMSO stock containing serial dilutions of the test compound (typically starting from a final concentration of 7.5 µM). The plate was preincubated for 10 minutes at 30° C. and the reaction initiated by addition of 10 µl of Aurora-2. Initial reaction rates were determined with a Molecular Devices SpectraMax Plus plate reader over a 10 minute time course. IC50 and Ki data were calculated from non-linear regression analysis using the Prism software package (GraphPad Prism version 3.0cx for Macintosh, GraphPad Software, San Diego Calif., USA).

Compound I-1 was found to inhibit Aurora A at a Ki value of 33 nM. Compounds of I-2 to I-4 and I-7 and I-8 were found to inhibit Aurora A at a Ki value of <0.5 µM.

Example 9

Aurora-1 (Aurora B) Inhibition Assay (Radiometric)

An assay buffer solution was prepared which consisted of 25 mM HEPES (pH 7.5), 10 mM MgCl$_2$, 0.1% BSA and 10% glycerol. A 22 nM Aurora-B solution, also containing 1.7 mM DTT and 1.5 mM Kemptide (LRRASLG), was prepared in assay buffer. To 22 µL of the Aurora-B solution, in a 96-well plate, was added 2 µl of a compound stock solution in DMSO and the mixture allowed to equilibrate for 10 minutes at 25° C. The enzyme reaction was initiated by the addition of 16 µl stock [γ-$^{33}$P]-ATP solution (~20 nCi/µL) prepared in assay buffer, to a final assay concentration of 800 µM. The reaction was stopped after 3 hours by the addition of 16 µL 500 mM phosphoric acid and the levels of $^{33}$P incorporation into the peptide substrate were determined by the following method.

A phosphocellulose 96-well plate (Millipore, Cat no. MAPHNOB50) was pre-treated with 100 µL of a 100 mM phosphoric acid prior to the addition of the enzyme reaction mixture (40 µL). The solution was left to soak on to the phosphocellulose membrane for 30 minutes and the plate subsequently washed four times with 200 µL of a 100 mM phosphoric acid. To each well of the dry plate was added 30

μL of Optiphase 'SuperMix' liquid scintillation cocktail (Perkin Elmer) prior to scintillation counting (1450 Microbeta Liquid Scintillation Counter, Wallac). Levels of non-enzyme catalyzed background radioactivity were determined by adding 16 μL of the 500 mM phosphoric acid to control wells, containing all assay components (which acts to denature the enzyme), prior to the addition of the [γ-$^{33}$P]-ATP solution. Levels of enzyme catalyzed $^{33}$P incorporation were calculated by subtracting mean background counts from those measured at each inhibitor concentration. For each Ki determination 8 data points, typically covering the concentration range 0-10 μM compound, were obtained in duplicate (DMSO stocks were prepared from an initial compound stock of 10 mM with subsequent 1:2.5 serial dilutions). Ki values were calculated from initial rate data by non-linear regression using the Prism software package (Prism 3.0, Graphpad Software, San Diego, Calif.).

Compounds I-1, I-2, I-4, and I-8 were found to inhibit Aurora B at a Ki value of >1.5 μM with the present assay condition. Compounds I-3 and I-7 were found to inhibit Aurora B at a Ki value of <0.5 μM with the present assay condition. Compounds I-5 and I-6 were not tested.

Example 10

Analysis of Cell Proliferation and Viability

Compounds were screened for their ability to inhibit cell proliferation and their effects on cell viability using Colo205 cells obtained from ECACC and using the assay shown below.

Colo205 cells were seeded in 96 well plates and serially diluted compound was added to the wells in duplicate. Control groups included untreated cells, the compound diluent (0.1% DMSO alone) and culture medium without cells. The cells were then incubated for 72 hrs at 37° C. in an atmosphere of 5% CO2/95% humidity.

To measure proliferation, 3 h prior to the end of the experiment 0.5 μCi of 3H thymidine was added to each well. Cells were then harvested and the incorporated radioactivity counted on a Wallac microplate beta-counter. Cell viability was assessed using Promega CellTiter 96AQ to measure MTS conversion. Dose response curves were calculated using either Prism 3.0 (GraphPad) or SoftMax Pro 4.3.1 LS (Molecular Devices) software.

While we have described a number of embodiments of this invention, it is apparent that our basic examples may be altered to provide other embodiments that utilize or encompass the compounds, methods, and processes of this invention. Therefore, it will be appreciated that the scope of this invention is to be defined by the appended claims.

We claim:
1. A compound of formula I:

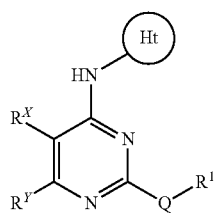

I or a pharmaceutically acceptable salt thereof, wherein:
Ht is

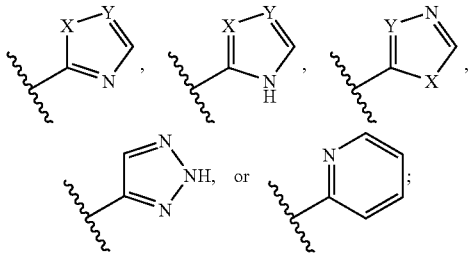

wherein said Ht is optionally and independently substituted with $R^2$ and $R^{2'}$, provided that Ht is not pyrazolyl or thiazolyl;
X is CH, N, O, or S;
Y is CH, N, O, or S;
Q is —O—, —NR'—, —S—, —C(=O)—, or —C(R')$_2$—;
$R^X$ is H or F;
$R^Y$ is —Z—$R^{10}$;
$R^1$ is T-(Ring D);
Ring D is a 5-7 membered monocyclic aryl or heteroaryl ring, wherein said heteroaryl has 1-4 ring heteroatoms selected from O, N, and S; Ring D can optionally be fused with Ring D';
Ring D' is a 5-8 aromatic, partially saturated, or fully unsaturated ring containing 0-4 ring heteroatoms selected from nitrogen, oxygen or sulfur;
Ring D and Ring D' are each independently and optionally substituted with 0-4 occurrences of oxo or —W—$R^5$;
each T is independently a $C_{1-4}$alkylidene chain or is absent;
$R^2$ is H, $C_{1-3}$alkyl, or cyclopropyl;
$R^{2'}$ is H;
each Z, and W is independently absent or a $C_{1-10}$alkylidene chain wherein up to six methylene units of the alkylidene chain are optionally replaced by V;
each V is selected from —O—, —C(=O)—, —S(O)—, —S(O)$_2$—, —S—, or —N($R^4$)—;
each $R^5$ is independently —R, -halo, —OR, —C(=O)R, —CO$_2$R, —COCOR, COCH$_2$COR, —NO$_2$, —CN, —S(O)R, —S(O)$_2$R, —SR, —N($R^4$)$_2$, —CON($R^7$)$_2$, —SO$_2$N($R^7$)$_2$, —OC(=O)R, —N($R^7$)COR, —N($R^7$)CO$_2$($C_{1-6}$aliphatic), —N($R^4$)N($R^4$)$_2$, —C=NN($R^4$)$_2$, —C=N—OR, —N($R^7$)CON($R^7$)$_2$, —N($R^7$)SO$_2$N ($R^7$)$_2$, —N($R^4$)SO$_2$R, or —OC(=O)N($R^7$)$_2$;
each R is H, a $C_{1-6}$aliphatic group, a $C_{6-10}$aryl ring, a heteroaryl ring having 5-10 ring atoms, or a heterocyclyl ring having 4-10 ring atoms; wherein said heteroaryl or heterocyclyl ring has 1-4 ring heteroatoms selected from nitrogen, oxygen, or sulfur; R is optionally substituted with 0-6 $R^9$;
each $R^4$ is —$R^7$, —COR$^7$, —CO$_2$R$^7$, —CON($R^7$)$_2$, or —SO$_2$R$^7$;
each $R^7$ is independently H or an optionally substituted $C_{1-6}$aliphatic group; or two $R^7$ on the same nitrogen are taken together with the nitrogen to form an optionally substituted 4-8 membered heterocyclyl or heteroaryl ring containing 1-4 heteroatoms selected from nitrogen, oxygen, or sulfur;
each $R^9$ is —R', -halo, —OR', —C(=O)R', —CO$_2$R', —COCOR', COCH$_2$COR', —NO$_2$, —CN, —S(O)R', —S(O)$_2$R', —SR', —N(R')$_2$, —CON(R')$_2$, —SO$_2$N (R')$_2$, —OC(=O)R', —N(R')COR', —N(R')CO$_2$($C_{1-6}$ aliphatic), —N(R')N(R')$_2$, —N(R')CON(R')$_2$, —N(R') SO$_2$N(R')$_2$, —N(R')SO$_2$R', —OC(=O)N(R')$_2$, =NN (R')$_2$, =N—OR', or =O;

each R¹⁰ is a 4-membered heterocyclic ring containing 1 heteroatom selected from O, N, and S; each R¹⁰ is optionally substituted with 0-6 occurrences of J;

each J is independently R, -halo, —OR, oxo, —C(=O)R, —CO₂R, —COCOR, —COCH₂COR, —NO₂, —CN, —S(O)R, —S(O)₂R, —SR, —N(R⁴)₂, —CON(R⁷)₂, —SO₂N(R⁷)2, —OC(=O)R, —N(R⁷)COR, —N(R⁷)CO₂(C₁₋₆aliphatic), —N(R⁴)N(R⁴)₂, =NN(R⁴)₂, =N—OR, —N(R⁷)CON(R⁷)₂, —N(R⁷)SO₂N(R⁷)₂, —N(R⁴)SO₂R, —OC(=O)N(R⁷)₂, or —OP(=O)(OR")₂; or 2 J groups, on the same atom or on different atoms, together with the atom(s) to which they are bound, form a 3-8 membered saturated, partially saturated, or unsaturated ring having 0-2 heteroatoms selected from O, N, or S; wherein 1-4 hydrogen atoms on the ring formed by the 2 J groups is optionally replaced with halo, C₁₋₃alkyl, or —O(C₁₋₃alkyl); or two hydrogen atoms on the ring are optionally replaced with oxo or a spiro-attached C₃₋₄cycloalkyl; wherein said C₁₋₃alkyl is optionally substituted with 1-3 fluorine;

each R' is independently H or a C₁₋₆aliphatic group; or two R', together with atom(s) to which they are bound, form a 3-6 membered carbocyclyl or a 3-6 membered heterocyclyl containing 0-1 heteroatoms selected from O, N, and S; and each R" is independently H or C₁₋₂alkyl.

2. The compound of claim 1, wherein Ht is

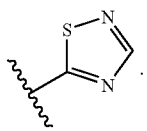 [SMILES: *c1ncns1]

3. The compound of claim 1, wherein Ht is

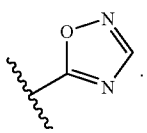 [SMILES: *c1ncno1]

4. The compound of claim 1, wherein Ht is

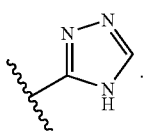

5. The compound of claim 1, wherein Ht is

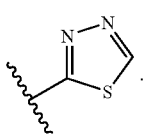

6. The compound of claim 1, wherein Ht is

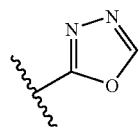

7. The compound of claim 1, wherein Ht is

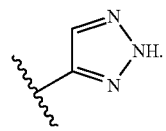 [SMILES: *c1cn[nH]n1]

8. The compound of claim 1, wherein Ht is

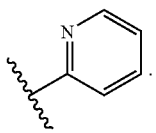

9. The compound of claim 1, wherein Ht is substituted as shown below:

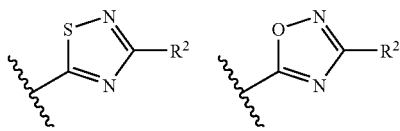

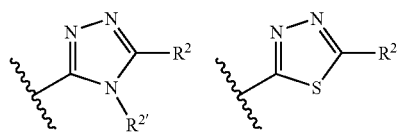

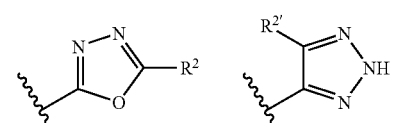

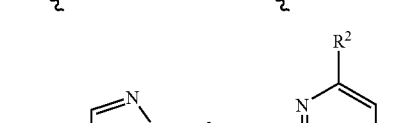

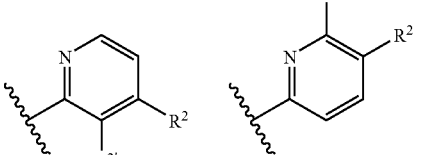 or

-continued

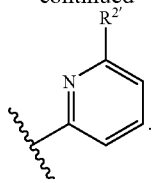

10. The compound of claim 9, wherein Q is —S—.
11. The compound of any one of claim 9, wherein Q is —O—.
12. The compound of any one of claim 11, wherein $R^2$ is H or $C_{1-3}$alkyl.
13. The compound of any one of claim 12, wherein $R^X$ is H.
14. The compound of any one of claim 13, wherein Ring D-D' is an 8-12 membered bicyclic aryl or heteroaryl containing 1-5 heteroatoms selected from nitrogen, oxygen, or sulfur.
15. The compound of claim 14, wherein Ring D-D' is a 6:6 ring system.
16. The compound of claim 15, wherein Ring D-D' is quinoline.
17. The compound of claim 14, wherein Ring D-D' is a 6:5 ring system.
18. The compound of claim 17, wherein said 6:5 ring system contains 2 nitrogen atoms.
19. The compound of claim 18, wherein Ring D-D' is a benzimidazole, indazole, or imidazopyridine ring.
20. The compound of claim 19, wherein Ring D-D' is a benzimidazole ring.
21. The compound of claim 13, wherein Ring D is a 5-6 membered monocyclic aryl or heteroaryl ring; and wherein D is not fused with D'.
22. The compound of claim 21, wherein Ring D is phenyl.
23. The compound of claim 22, wherein Ring D is phenyl, wherein the phenyl is independently substituted with one or two substituents selected from -halo and —N($R^7$)$CO_2$($C_{1-6}$aliphatic).
24. The compound of claim 22, wherein Ring D is phenyl, wherein the phenyl is independently substituted with —F and —$NHCO_2$($C_{1-3}$aliphatic).
25. The compound of claim 22, wherein Ring D is phenyl, wherein the phenyl is independently substituted with —F and —$NHCO_2$(cyclopropyl).
26. The compound of claim 22, wherein Ring D is

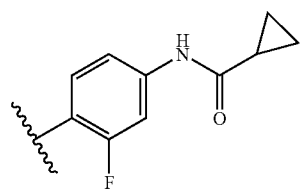

27. The compound of claim 26, wherein Z is absent.
28. The compound of any one of claim 26, wherein Z is a $C_{1-6}$alkylidene chain wherein 1-2 methylene units of Z is optionally replaced by O, —N($R^4$)—, or S.
29. The compound of claim 28, wherein Z is a $C_{1-4}$alkylidene chain.
30. The compound of claim 26, wherein $R^{10}$ is an optionally substituted azetidine.

31. The compound of claim 30, wherein $R^Y$ is represented by formula i:

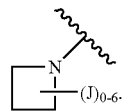

i

32. The compound of claim 30, wherein $R^Y$ is represented by formula ii-a:

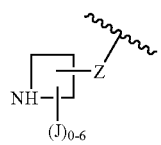

ii-a

33. The compound of claim 1 selected from the following:

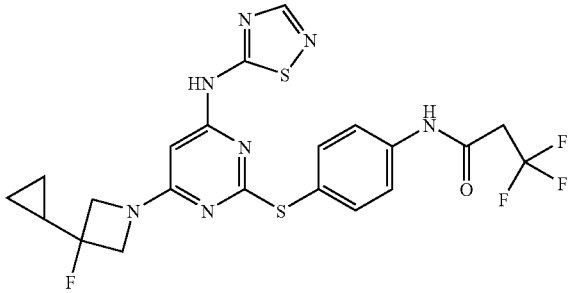

I-1

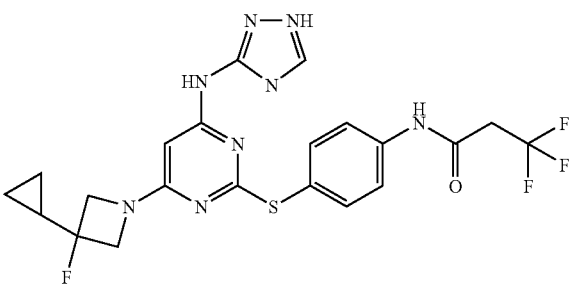

I-2

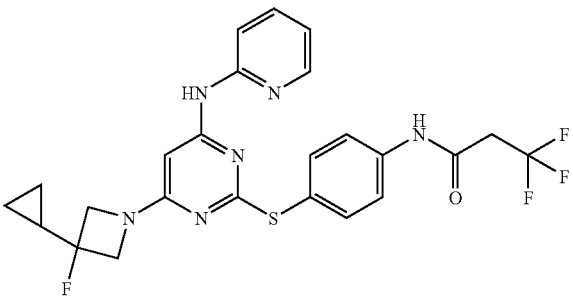

I-3

I-4

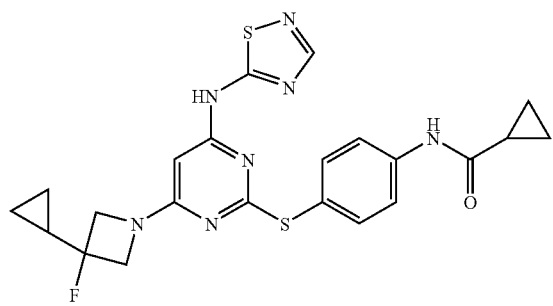

I-5

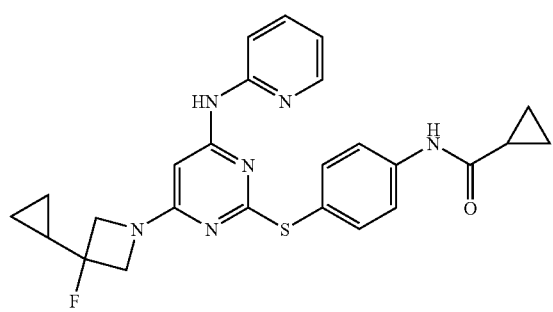

I-6

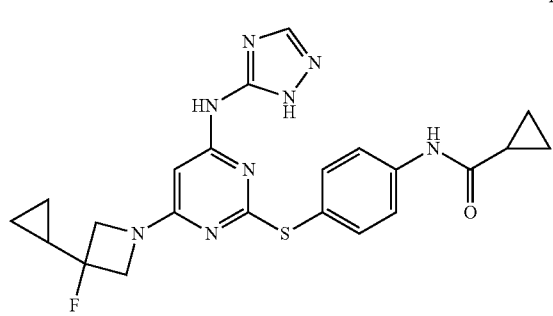

I-7

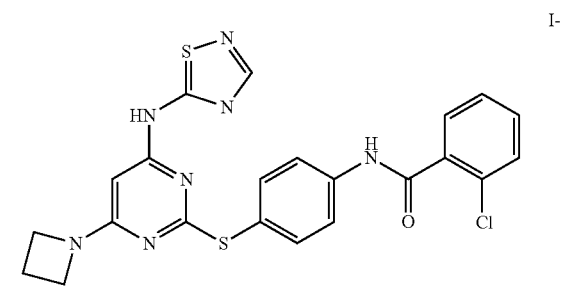

I-8

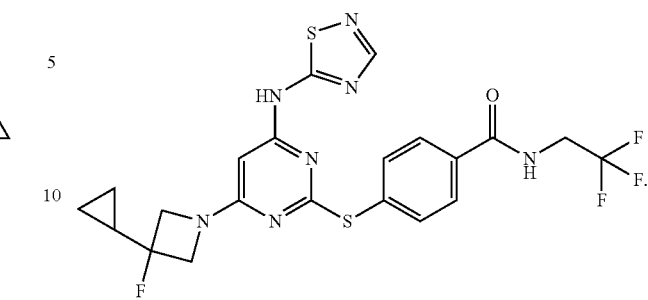

34. A composition comprising a compound of formula I:

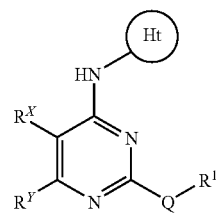

I or a pharmaceutically acceptable salt thereof, and a pharmaceutically acceptable carrier, wherein the variables are defined according to claim 1.

35. A method of treating a proliferative disorder in a patient comprising the step of administering to said patient a compound of formula I:

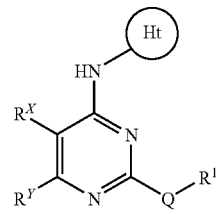

I or a pharmaceutically acceptable salt thereof, wherein the variables are defined according to claim 1; and the proliferative disorder is colon cancer.

* * * * *